(12) United States Patent
Dechev et al.

(10) Patent No.: US 11,564,815 B2
(45) Date of Patent: Jan. 31, 2023

(54) UPPER ARM PROSTHETIC APPARATUS AND SYSTEMS

(71) Applicant: Victoria Hand Project, Victoria (CA)

(72) Inventors: Nikolai Dechev, Victoria (CA); Michael Carl Veikko Peirone, West Vancouver (CA); Nicholas James Whyte, Victoria (CA); Kelly Marie Knights, Calgary (CA); Derek John Bell, Kamloops (CA)

(73) Assignee: Victoria Hand Project, Victoria (CA)

( * ) Notice: Subject to any disclaimer, the term of this patent is extended or adjusted under 35 U.S.C. 154(b) by 433 days.

(21) Appl. No.: 16/574,000

(22) Filed: Sep. 17, 2019

(65) Prior Publication Data

US 2021/0077280 A1    Mar. 18, 2021

(51) Int. Cl.
| | |
|---|---|
| *A61F 2/58* | (2006.01) |
| *A61F 2/80* | (2006.01) |
| *A61F 2/70* | (2006.01) |
| *A61F 2/78* | (2006.01) |
| *A61F 2/54* | (2006.01) |
| *A61F 2/68* | (2006.01) |

(52) U.S. Cl.
CPC .............. *A61F 2/586* (2013.01); *A61F 2/585* (2013.01); *A61F 2/70* (2013.01); *A61F 2/80* (2013.01); *A61F 2/582* (2013.01); *A61F 2/588* (2013.01); *A61F 2002/546* (2013.01); *A61F 2002/587* (2013.01); *A61F 2002/6836* (2013.01); *A61F 2002/7862* (2013.01)

(58) Field of Classification Search
CPC .. A61F 2/54; A61F 2/582; A61F 2/583; A61F 2/585; A61F 2/586; A61F 2/588; A61F 2/70; A61F 2/76; A61F 2/80; A61F 2002/546; A61F 2002/587; A61F 2002/6836; A61F 2002/7862
See application file for complete search history.

(56) References Cited

U.S. PATENT DOCUMENTS

| | | | |
|---|---|---|---|
| 42,515 | A | 4/1864 | Spellerberg |
| 51,238 | A | 11/1865 | Spellerberg |
| 1,225,415 | A | 5/1917 | Cronemiller |
| 1,247,077 | A | 11/1917 | Caron |

(Continued)

FOREIGN PATENT DOCUMENTS

| | | | |
|---|---|---|---|
| CN | 105056544 A | 11/2015 | |
| DE | 102012012173 A1 * | 12/2013 | ............... A61F 2/60 |

(Continued)

OTHER PUBLICATIONS

Mottard, Annick. Underactuated tendon-driven robotic/prosthetic hands: design issues. Universite Laval, Quebec. (Year: 2017).*

(Continued)

*Primary Examiner* — Christie L Bahena

(57) ABSTRACT

Various aspects of upper arm prosthetic system for a human subject having a body and a partial arm are described. According to one aspect, the system may comprise any one or more of a force amplification apparatus, a terminal unit apparatus, and/or an adjustable elbow apparatus. Each apparatus may be body-powered and/or comprise 3D printable structures. Related upper arm prosthetic apparatus, kits, methods, and systems also are described.

20 Claims, 25 Drawing Sheets

(56) References Cited

U.S. PATENT DOCUMENTS

| | | | |
|---|---|---|---|
| 1,273,461 A | 7/1918 | Corley | |
| 1,298,502 A | 3/1919 | Henning | |
| 1,324,564 A | 12/1919 | Pringle | |
| 1,347,004 A | 7/1920 | Beck | |
| 1,365,646 A | 1/1921 | Adams | |
| 1,366,453 A | 1/1921 | Henning | |
| 1,385,817 A | 7/1921 | Dilworth | |
| 1,402,709 A | 1/1922 | Blatchford | |
| 1,458,923 A | 6/1923 | Anderson | |
| 1,465,933 A | 8/1923 | Dedic | |
| 1,466,163 A | 8/1923 | Harris | |
| 1,484,913 A | 2/1924 | Surry | |
| 1,507,680 A | 9/1924 | Pecorella et al. | |
| 1,507,681 A | 9/1924 | Pecorella et al. | |
| 1,507,682 A | 9/1924 | Pecorella et al. | |
| 1,507,683 A | 9/1924 | Pecorella et al. | |
| 1,569,286 A | 1/1926 | Laherty | |
| 1,630,277 A | 5/1927 | Smith | |
| 1,644,833 A | 10/1927 | Hoare | |
| 1,742,269 A | 1/1930 | McElroy | |
| 1,792,183 A | 2/1931 | Pecorella | |
| 1,989,960 A | 2/1935 | Wheeler et al. | |
| 2,285,885 A | 6/1942 | Becker | |
| 2,287,781 A | 6/1942 | Carnes | |
| 2,301,009 A | 11/1942 | Becker | |
| 2,364,313 A | 12/1944 | Pecorella | |
| 2,425,154 A | 8/1947 | Hibbard | |
| 2,433,301 A | 12/1947 | Simpson | |
| 2,457,305 A | 12/1948 | Dale | |
| 2,464,577 A | 3/1949 | Hobbs | |
| 2,493,776 A | 1/1950 | Pecorella et al. | |
| 2,516,791 A | 7/1950 | Motis et al. | |
| 2,532,732 A | 12/1950 | Sansbury | |
| 2,535,489 A | 12/1950 | Edwards | |
| 2,537,551 A | 1/1951 | Sansbury | |
| 2,540,374 A | 2/1951 | Motis | |
| 2,540,375 A | 2/1951 | Motis | |
| 2,549,716 A | 4/1951 | Simpson | |
| 2,549,792 A | 4/1951 | Fletcher | |
| 2,553,827 A | 5/1951 | Mason | |
| 2,553,830 A | 5/1951 | Motis | |
| 2,556,524 A | 6/1951 | Drennon | |
| 2,561,383 A | 7/1951 | Larkins et al. | |
| 2,572,914 A | 10/1951 | Chapman et al. | |
| 2,582,234 A | 1/1952 | Conzelman, Jr. et al. | |
| 2,592,842 A | 4/1952 | Alderson | |
| 2,626,398 A | 1/1953 | Grindle et al. | |
| 2,652,570 A | 9/1953 | Sargeson | |
| 2,654,891 A | 10/1953 | Robinson | |
| 2,669,727 A | 2/1954 | Opuszenski | |
| 2,706,296 A | 4/1955 | Fletcher et al. | |
| 2,847,678 A | 8/1958 | Opuszenski | |
| 2,853,711 A * | 9/1958 | Becker | A61F 2/583 623/63 |
| 2,859,450 A | 11/1958 | Becker | |
| 2,867,819 A | 1/1959 | George | |
| 2,885,686 A | 5/1959 | Giaimo | |
| 3,026,534 A * | 3/1962 | Brown | A61F 2/583 623/64 |
| 3,107,358 A | 10/1963 | Prout | |
| 3,159,847 A | 12/1964 | Prout | |
| 3,258,784 A | 7/1966 | Brown | |
| 3,382,506 A | 5/1968 | Collins et al. | |
| 3,413,658 A | 12/1968 | Becker | |
| 3,432,198 A | 3/1969 | Connor | |
| 3,694,021 A | 9/1972 | Mullen | |
| 4,038,706 A | 8/1977 | Ober et al. | |
| 4,040,130 A | 8/1977 | Laure | |
| 4,067,070 A | 1/1978 | Seamone et al. | |
| 4,074,367 A | 2/1978 | Loveless | |
| 4,084,267 A | 4/1978 | Zadina | |
| 4,094,016 A | 6/1978 | Eroyan | |
| 4,167,044 A | 9/1979 | Girard | |
| 4,180,870 A | 1/1980 | Radulovic et al. | |
| 4,232,405 A | 11/1980 | Janovsky | |
| 4,291,421 A | 9/1981 | Massey et al. | |
| 4,310,932 A | 1/1982 | Nader et al. | |
| 4,364,593 A | 12/1982 | Maeda | |
| 4,521,924 A | 6/1985 | Jacobsen et al. | |
| 4,604,098 A | 8/1986 | Seamone et al. | |
| 4,651,719 A | 3/1987 | Funk et al. | |
| 4,685,924 A | 8/1987 | Massey | |
| 4,685,928 A | 8/1987 | Yaeger | |
| 4,685,929 A | 8/1987 | Monestier | |
| 4,792,338 A | 12/1988 | Rennerfelt | |
| 4,865,613 A | 9/1989 | Rizzo | |
| 4,921,293 A | 5/1990 | Ruoff et al. | |
| 4,946,380 A | 8/1990 | Lee | |
| 4,957,281 A | 9/1990 | Christolear, Jr. | |
| 4,990,162 A | 2/1991 | LeBlanc et al. | |
| 5,080,682 A | 1/1992 | Schectman | |
| 5,104,121 A | 4/1992 | Webb | |
| 5,314,500 A | 5/1994 | Weddendorf | |
| 5,800,571 A | 9/1998 | Carlson et al. | |
| 5,800,572 A | 9/1998 | Loveall | |
| 5,888,235 A | 3/1999 | Jacobsen et al. | |
| 6,115,898 A | 9/2000 | Sawdon | |
| 6,513,198 B2 | 2/2003 | Lu | |
| 6,896,704 B1 | 5/2005 | Higuchi et al. | |
| 6,913,627 B2 | 7/2005 | Matsuda | |
| 7,087,092 B1 | 8/2006 | Landsberger | |
| 7,112,221 B2 | 9/2006 | Harris | |
| 7,361,197 B2 | 4/2008 | Winfrey | |
| 7,655,051 B2 | 2/2010 | Stark | |
| 7,867,287 B2 | 1/2011 | Puchhammer | |
| 8,132,291 B2 | 3/2012 | Tsai et al. | |
| 8,343,234 B2 | 1/2013 | Puchhammer | |
| 8,608,396 B2 | 12/2013 | Mekid | |
| 8,684,621 B2 | 4/2014 | Forthaus et al. | |
| 8,795,387 B1 | 8/2014 | Razink | |
| 9,320,621 B2 | 4/2016 | Iversen et al. | |
| 9,572,688 B2 | 2/2017 | Puchhammer et al. | |
| 10,219,919 B2 | 3/2019 | Belter et al. | |
| 10,271,966 B2 | 4/2019 | Glasgow | |
| 2005/0006915 A1 | 1/2005 | Matsuda | |
| 2005/0021155 A1 | 1/2005 | Brimalm | |
| 2006/0129248 A1 | 6/2006 | Stark | |
| 2006/0224249 A1 | 10/2006 | Winfrey | |
| 2007/0173955 A1 | 7/2007 | Archer et al. | |
| 2007/0213842 A1 | 9/2007 | Simmons | |
| 2008/0188952 A1 | 8/2008 | Veatch et al. | |
| 2008/0262634 A1 | 10/2008 | Puchhammer | |
| 2008/0262636 A1 | 10/2008 | Puchhammer | |
| 2008/0319553 A1 | 12/2008 | Pucchammer | |
| 2010/0274365 A1 | 10/2010 | Evans et al. | |
| 2012/0146352 A1 | 6/2012 | Haslinger | |
| 2012/0150322 A1 | 6/2012 | Goldfarb et al. | |
| 2013/0046395 A1 | 2/2013 | Mcleary | |
| 2014/0171846 A1 | 6/2014 | Bonutti et al. | |
| 2015/0230941 A1 | 8/2015 | Jury | |
| 2015/0297367 A1 | 10/2015 | Baba et al. | |
| 2015/0351935 A1 | 12/2015 | Donati et al. | |
| 2016/0166409 A1 | 6/2016 | Goldfarb et al. | |
| 2016/0374833 A1 | 12/2016 | Dechev et al. | |
| 2017/0049583 A1* | 2/2017 | Belter | A61F 2/583 |
| 2018/0098862 A1 | 4/2018 | Kuiken et al. | |
| 2018/0133028 A1 | 5/2018 | Poirters | |
| 2018/0140441 A1 | 5/2018 | Poirters | |
| 2018/0311827 A1 | 11/2018 | Bicchi et al. | |

FOREIGN PATENT DOCUMENTS

| | | | | |
|---|---|---|---|---|
| DE | 102015116133 B3 | 1/2017 | | |
| EP | 0079593 B1 | 2/1986 | | |
| EP | 0635247 B1 | 11/1998 | | |
| EP | 1457294 A1 | 9/2004 | | |
| FR | 2665833 A1 | 2/1992 | | |
| FR | 2822404 B1 | 9/2002 | | |
| GB | 157256 A * | 6/1921 | | A61F 2/582 |
| GB | 2278281 A | 11/1994 | | |
| JP | 2014213199 A | 11/2014 | | |
| KR | 101738098 B1 | 5/2017 | | |
| SU | 409715 A1 | 1/1974 | | |
| SU | 1975 * | 9/1974 | | |

(56) References Cited

FOREIGN PATENT DOCUMENTS

| | | | |
|---|---|---|---|
| WO | WO-8501437 A1 * | 9/1984 | |
| WO | 1985001437 A1 | 4/1985 | |
| WO | 2000071060 A1 | 11/2000 | |
| WO | 2003017880 A1 | 3/2003 | |
| WO | 2007076763 A2 | 7/2007 | |
| WO | WO-2012021823 A1 * | 2/2012 | A61F 2/80 |
| WO | 2013076683 A1 | 5/2013 | |
| WO | WO-2013076683 A1 * | 5/2013 | A61F 2/583 |
| WO | 2013185231 A1 | 12/2013 | |
| WO | 2017111582 A1 | 6/2017 | |
| WO | 2017212128 A1 | 12/2017 | |

OTHER PUBLICATIONS

Knights, Kelly. A Helping Hand to Those in Need-Improving the World with 3D Printing. 3D Heals blog. Jan. 13, 2019. (Year: 2019).*
Youtube clip 1,2, 3. Rick at the University of Victoria. (Year: 2018).*
Facebookl. Victoria Hand Project. Facebook post Mar. 15, 2018 at 6:00PM. (Year: 2018).*
Facebook2. Victoria Hand Project. Posted Aug. 28, 2018 at 12:09PM. (Year: 2018).*
Fillauer catalog. p. 88. (Year: 2017).*
Youtube2. Clips 1, 2. Victoria Hand Project. (Year: 2015).*
Youtube3. Clips 1, 2, 3. Affordable 3D Printed Prosthetic: Victoria Hand Projectl Get Connected. (Year: 2016).*
Cuellar et al., Ten guidelines for the design of non-assembly mechanisms: The case of 3D-printed prosthetic hands, Proceedings of the Institution of Mechanical Engineers, Part H: Journal of Engineering in Medicine, Aug. 16, 2018, 10, vol. 232, Issue 9, 095441191879473. 10.1177/0954411918794734, 2018.
Bethanylc, E-NABLE: How to Assemble the Isabella Arm by FATHOM, URL: https://www.instructables.com/id/E-NABLE-How-to-assemble-the-Isabella-Arm-by-FATHOM/, Oct. 16, 2015.
Phillipe Marin, whippletree in hand (e-Nable), URL: https://www.youtube.com/watch?v=5zETGP9-c5A, Uploaded Nov. 6, 2016.
John Diamond, How a whippletree works in an e-NABLE hand, URL: https://www.youtube.com/watch?v=dW5B_CeJtd8, Uploaded Sep. 13, 2015.
Victoria Hand Project, Facebook, Oct. 12, 2016, available at: https://www.facebook.com/victoriahandproject/photos/a.1584810318449494/1731835533746971/ (last accessed: Feb. 15, 2022).
Victoria Hand Project, Facebook, Mar. 7, 2017, available at: https://www.facebook.com/victoriahandproject/posts/1797284497202074 (last accessed: Feb. 15, 2020).
Victoria Hand Project, Facebook, Mar. 15, 2018, available at: https://www.facebook.com/victoriahandproject/posts/1968932906703898 (last accessed: Feb. 15, 2022).
Victoria Hand Project, Facebook, Aug. 11, 2017, available at: https://www.facebook.com/victoriahandproject/posts/1870329629897560 (last accessed: Feb. 15, 2022).
Victoria Hand Project, Facebook, Jul. 4, 2017, available at: https://www.facebook.com/victoriahandproject/posts/1852565468340643 (last accessed: Feb. 15, 2022).
Victoria Hand Project, Facebook, Jan. 16, 2018, available at: https://www.facebook.com/victoriahandproject/posts/1939847636279092 (last accessed: Feb. 15, 2022).
Victoria Hand Project, Facebook, Nov. 16, 2017, available at: https://www.facebook.com/victoriahandprojects/posts/1911363212460868 (last accessed: Feb. 15, 2022).
Victoria Hand Project, Facebook, Nov. 30, 2017, available at: https://www.facebook.com/victoriahandproject/posts/1917910715139451 (last accessed: Feb. 15, 2022).
Victoria Hand Project, Facebook, Dec. 16, 2017, available at: https://www.facebook.com/victoriahandproject/posts/1923540691243120 (last accessed: Feb. 15, 2022).
Victoria Hand Project, Facebook, Jan. 4, 2018, available at: https://www.facebook.com/victoriahandproject/posts/1934287786835077 (last accessed: Feb. 15, 2022).
Victoria Hand Project, "Victoria Hand Project: 3D Printed Prostheses for Guatemala and Nepal", YouTube, Jul. 22, 2015, available at: https://www.youtube.com/watch?v=clVHWrOACTk (last accessed: Feb. 15, 2022).
"The Limbitless Arm," Enabling the Future, Aug. 25, 2014, available at: http://enablingthefuture.org/upper-limb-prosthetics/the-limbitless-arm/ (last accessed: Feb. 15, 2022).
"The Raptor hand by e-NABLE," MakerBot Thingiverse, Sep. 29, 2014, available at: http://www.thingiverse.com/thing:476403 (last accessed: Feb. 15, 2022).
"The Rit Arm," Enabling the Future website, Dec. 9, 2014, available at: http://enablingthefuture.org/upper-limb-prosthetics/rit-arm/ (last accessed: Feb. 15, 2022).
Andrew Wheeler, "Victoria Hand Project's Mission to Increase Developing World Access to Prosthetics," 3D Printing Industry, Jul. 15, 2015, 15 pages, available at: https://3dprintingindustry.com/news/victoria-hand-projects-mission-to-increase-developing-world-access-to-prosthetics-53432/ (last accessed: Feb. 15, 2022).
Angie MacDonald, "Changing lives in developing countries with 3D printed prosthetics," Ultimaker, Nov. 2016, 8 pages.
Bob Radocy, "TRS Product Catalog," Jan. 2015, available online at: http://www.prosthetics.com/wp-content/uploads/2015/10/TRS_CAT15-en.pdf (last accessed: Feb. 15, 2022).
Brent Crane, "Brothers Craft 3D-printed Prostheses for Amputees," The Phnom Penh Post, May 26, 2016, 5 pages, available at: https://www.phnompenhpost.com/national/brothers-craft-3d-printed-prostheses-amputees?fbclid=IwAR1kZQnKWe01ua4yzgvEawdkSaROPhkTgzfofFv3cf_CfnWMwAtdLVf_ETo (last accessed: Feb. 15, 2022).
Christian Silva, "3D printed Mechanical Arm Enable Promimetic Fabrilab," YouTube, Uploaded Sep. 11, 2017, available at: https://www.youtube.com/watch?v=HS8D0MYCDKg (last accessed: Feb. 15, 2022).
Christine Van Reeuwyk, "UVic Project Rebuilds Lives One Hand at a Time," TODAY IN BC, Mar. 17, 2017, 4 pages, available at: https://www.todayinbc.com/news/uvic-project-rebuilds-lives-one-hand-at-a-time/ (last accessed: Feb. 15, 2022).
Colin Pischke, "Victoria Hand Project—Guest Post", Pym3d, Mar. 19, 2017, 3 pages, available at: https://www.printyourmind3d.ca/blogs/articles/victoria-hand-project (last accessed: Feb. 15, 2022).
Cormac O'Brien, "Victoria Hand Project gets tapped for half-million-dollar grant", Martlet, Mar. 23, 2017, 6 pages, available at: http://www.martlet.ca/victoria-hand-project-gets-tapped-for-half-million-dollar-grant/ (last accessed: Feb. 15, 2022).
"UVic Engineers 3D-Print New Hand for Sidney man", CTV News Vancouver Island, available at: https://vancouverisland/ctvnews.ca/video?clipID=971219&fbclid=IwAR2d2-NmaSOkzhWc4dkJJZttOtuDB_FMMm4TfeAXEn0Y2V_usOHN86dP60 (last accessed: Feb. 15, 2022).
De Laurentis et al., "Mechanical Design of a Shape Memory Alloy Actuated Prosthetic Hand," Est. Pub. Date 2022, pp. 34, available at: http://engineering.nyu.edu/mechatronics/Control_Lab/bck/Padmini/Nano/Mavroidis/THC.pdf (last accessed: Feb. 15, 2022).
Dechev et al., "Multiple Finger, Passive Adaptive Grasp Prosthetic Hand," Journal of Mechanism and Machine Theory, 2001, pp. 1157-1173, vol. 36, Elsevier Science Ltd.
Hanna Watkin, "The Victoria Hand Project Uses 3D Printing to Create Ergonomic Prosthetics", All3DP, Dec. 8, 2016, 5 pages, available at: https://all3dp.com/the-victoria-hand-project-uses-3d-printing-to-create-ergonomic-prosthetics/ (last accessed: Feb. 15, 2022).
Jeffrey Joiner, "Guidelines for the design of electromechanical hands and incorporation of compliant fingertips", 1994, OCLC No. 1017514454, National Library of Canada, Ottawa, Canada.
Justine Hunter, "Forging prosthetics from plastic for a pittance", The Globe and Mail, Dec. 28, 2016, 2 pages, available at: https://www.theglobeandmail.com/news/british-columbia/victoria-hand-project-is-forging-prosthetics-from-plastic-for-a-pittance/

(56) References Cited

OTHER PUBLICATIONS article33444630/?fbclid=IwAR3xi-t3U9DwQt7gLEMdpZfS2_xhWAo7DvIAmKX2sNbs3lzoP05dk6tK5U (last accessed: Feb. 15, 2022).
Lisa O'Brien, "The Winston Churchill Memorial Trust of Australia", The Winston Churchill Memorial Trust, Jun. 9, 2018, 28 pages.
Neeta Garcha, "Lending a helping hand: Victoria non-profit in the running for huge Google grant", Global News, Mar. 9, 2017, 8 pages, available at: https://globalnews.ca/news/3297918/lending-a-helping-hand-victoria-non-profit-in-the-running-for-huge-google-grant/?fbclid=IwAR3MKus2OyMXLE7HoAQpbeMz4rXKZRO9CFvKkigomal1lesWX9pPuF2CPxo (last accessed: Feb. 15, 2022).
Nick Dechev, "Victoria Hand Project Info Video", Vimeo, Jul. 14, 2015, 2 pages, available at: https://vimeo.com/133500986 (last accessed: Feb. 15, 2022).
"MyolinoWrist 2000," Ottobock, Est. Pub. Date. 2013, 3 pages, available at: https://shop.ottobock.us/Prosthetics/Upper-Limb-Prosthetics/Myo-Hands-and-Components/Myo-Wrist-Units-and-Rotation/MyolinoWrist-2000/p/10V51~52#product-documents-section (last accessed: Feb. 15, 2022).
Rochester Institute of Technology, "e-NABLE—volunteers offer prosthetic hands made for children by 3D printers", Jun. 23, 2014, YouTube, available at: https://www.youtube.com/watch?v=T9nngOrdPkg (last accessed: Feb. 15, 2022).
Sarah Anderson Goehrke, "Victoria Hand Project—Offering Advanced, Affordable 3D Printed Upper-Limb Prostheses", 3dprint.com, Jul. 13, 2015, 6 pages, available at: https://3dprint.com/80946/victoria-hand-project/ (last accessed: Feb. 15, 2022).
Susan Hall, "Victoria Hand Project: Applying 3D Printing to Prosthetics", The New Stack, Jun. 21, 2018, 13 pages, available at: https://thenewstack.io/victoria-hand-project-applying-3d-printing-to-prosthetics/ (last accessed: Feb. 15, 2022).
"The Raptor Hand", Enabling the Future, Est. Pub. Date Sep. 29, 2015, 12 pages, available at: https://enablingthefuture.org/upper-limb-prosthetics/the-raptor-hand/ (last accessed: Feb. 15, 2022).
"The Victoria Hand Project: Making a World of Difference ~Nick Dechev, Ph.D.", The Canadian Club of Victoria, Mar. 16, 2017, 4 pages, available at: https://thecanadianclubofvictoria.com/event/test2/ (last accessed: Feb. 15, 2022).
Travis Paterson, "3D printers make Victoria Hand Project a reality", Victoria News, Nov. 10, 2017, 3 pages, available at: https://www.vicnews.com/news/3d-printers-make-victoria-hand-project-a-reality/?fbclid=IwAR21xxhqVnkPBM1BqWaGdF0qYwGhRkHH31edrCuTs5Tam_Hmpkr3peJiTO4 (last accessed: Feb. 15, 2022).
VICHANDPROJECT, Instagram, Feb. 26, 2018, available at: https://www.instagram.com/p/BfrsW24l2gn/?utm_source=ig_web_copy_link (last accessed: Feb. 15, 2022).
VICHANDPROJECT, Instagram, Jul. 4, 2017, available at: https://www.instagram.com/p/BWIqE9_FpAw/?utm_source=ig_web_copy_link (last accessed: Feb. 15, 2022).
VICHANDPROJECT, Instagram, Mar. 8, 2017, available at: https//www.instagram.com/p/BRYrghjFfl3/?utm_source=ig_web_copy_link (last accessed: Feb. 15, 2022).
Victoria Hand Project, "Victoria Hand Project Guatemala Feb. 2016 Trials", YouTube, Sep. 9, 2016, available at: https://www.youtube.com/watch?v=rVlePGFRcel (last accessed: Feb. 15, 2022).
Victoria Hand Project, Facebook, Nov. 18, 2017, available at: https://www.facebook.com/victoriahandproject/posts/1911761752421014 (last accessed: Feb. 15, 2022).
Victoria Hand Project, "One Hand Challenge!", YouTube, Dec. 4, 2015, available at: https://www.youtube.com/watch?v=a6E2Tr7Bprg (last accessed: Feb. 15, 2022).
Limbcare Nepal, Facebook, Aug. 26, 2018, available at: https://www.facebook.com/victoriahandproject/posts/2088954921368362 (last accessed: Feb. 15, 2022).
Victoria Hand Project, "Victoria Hand Project—Fundraiser for Canadian Amputees (Jan. 2018)", YouTube, Jan. 15, 2018, available at: https://www.youtube.com/watch?v=fMnj6KLqZ-U (last accessed: Feb. 15, 2022).
Victoria Hand Project, Facebook, Jan. 22, 2018, available at: https://www.facebook.com/victoriahandproject/videos/1943073702623152/ (last accessed: Feb. 15, 2022).
Victoria Hand Project, "Victoria Hand 3D Printed Prosthetic", YouTube, Jul. 10, 2015, available at: https://www.youtube.com/watch?v=t0ozZqQH5N8 (last accessed: Feb. 15, 2022).
Victoria Hand Project, Facebook, Jul. 11, 2015, available at: https://www.facebook.com/victoriahandproject/posts/1583265998603926 (last accessed: Feb. 15, 2022).
Victoria Hand Project, Facebook, Mar. 27, 2017, available at https://www.facebook.com/victoriahandproject/photos/a.1584810318449494/1806202796310244/ (last accessed: Feb. 15, 2022).
Victoria Hand Project, "Victoria Hand Project 3D Printed Prosthetic Haiti & Cambodia", YouTube, Sep. 9, 2016, available at: https://www.youtube.com/watch?v=YhhtMGKA-zs (last accessed: Feb. 15, 2022).
Victoria Hand Project, "Victoria Hand Project 3D Printed Prosthetic", YouTube, Feb. 17, 2016, available at: https://www.youtube.com/watch?v=uSd9uxlc5Sw (last accessed: Feb. 15, 2022).
Victoria Hand Project, Facebook, Mar. 24, 2017, available at: https://www.facebook.com/victoriahandproject/photos/a.1584810318449494/1804903939773463/ (last accessed: Feb. 15, 2022).
Victoria Hand Project, "Features of the Victoria Hand and how it works!", YouTube, Jan. 15, 2018, available at: https://www.youtube.com/watch?v=sUXGkAYWEa0 (last accessed: Feb. 15, 2022).
Victoria Hand Project, Facebook, Oct. 6, 2017, available at: https://www.facebook.com/victoriahandproject/posts/1893825434214646 (last accessed: Feb. 15, 2022).
Victoria Hand Project, Facebook, Nov. 15, 2017, available at: https://www.facebook.com/victoriahandprojects/posts/1910947722502417 (last accessed: Feb. 15, 2022).
Victoria Hand Project, Facebook, Mar. 3, 2018, available at: https://www.facebook.com/victoriahandproject/posts/1962961727301016 (last accessed: Feb. 15, 2022).
Victoria Hand Project, Facebook, Jan. 25, 2018, available at: https://www.facebook.com.victoriahandproject/posts/1944350352495487 (last accessed: Feb. 15, 2022).
Victoria Hand Project, Facebook, Dec. 13, 2017, available at: https://www.facebook.com/victoriahandproject/posts/1923538287910027 (last accessed: Feb. 15, 2022).
Victoria Hand Project, Facebook, Feb. 2, 2017, available at: https://www.facebook.com/victoriahandproject/photos/a.1584810318449494/1782448592018898/ (last accessed: Feb. 15, 2022).
Victoria Hand Project, "The Making of the Victoria Hand: A Functional, Low-Cost Prosthesis", YouTube, Jul. 22, 2015, available at: https://www.youtube.com/watch?v=9Rkf-K7oylw (last accessed: Feb. 15, 2022).

* cited by examiner

UPPER ARM PROSTHETIC APPARATUS AND SYSTEMS

BACKGROUND

1. Field

Aspects of the present disclosure generally relate to upper arm prosthetic apparatus and systems. Particular aspects are configured for use by smaller humans, including many women and children.

2. Description of Related Art

Various prosthetic hands may be worn on a distal end of an amputated arm to replace functions lost due to a hand deficiency. There are many known prosthetic hand designs, going back hundreds of years. Some historical designs were used for body balance and/or for cosmetic purposes. Most modern prosthetic hand designs allow for functional articulations and gripping of objects in addition to cosmetic appearance. Generally speaking, there are two basic types of modern prosthetic hands: (i) body-powered hands, including split-hook systems; and (ii) electric-powered hands, including electro-mechanical systems.

Electric-powered prosthetic hands may offer enhanced capabilities, but they are typically much more expensive to acquire, fit, and maintain due to their inherent complexity. Because of these additional expenses, most children are provided with body-powered prosthetic hands, typically a smaller version of an adult prosthetic hand. This is especially true in less developed countries. But the comparatively smaller size and strength of a child's body may frustrate usage of such prosthetics, making them difficult to operate and often causing premature abandonment of the prosthetic by the child. Maintaining a proper fit of the prosthetic also may be frustrated by the child's growing body, and provide yet another reason for abandonment. Similar frustrations also may be experience by many smaller humans, including many adult women and other persons of a smaller stature.

Further improvements are required to make body-powered prosthetic hands more accessible to smaller humans, including women and children. Aspects of this disclosure may solve these and related problems.

SUMMARY

Numerous aspects are described in this disclosure. One aspect is an upper arm prosthetic system for a human subject having a body and a partial arm extending from the body. The system may comprise any one or more of a force amplification apparatus, a terminal unit apparatus, and/or an adjustable elbow apparatus, individually or together, each of which may comprise 3D printable structures.

In some aspects, the force amplification apparatus may comprise structures defining: a support wearable on the partial arm; and a force amplifier rotatably engaged with the support and configured to receive input forces from an input member engageable with a harness wearable on the body, amplify the input forces into output forces, and transfer the output forces to an output member engageable with a terminal unit wearable on a distal portion of the partial arm.

In some aspects, the terminal unit apparatus may comprise structures defining: a socket wearable on a distal portion of the partial arm; a hand body engageable with the socket; force transfer elements engageable with the output member; and finger digits rotatably engaged with the hand body and the force transfer elements.

When the harness, the support, and the socket are worn, the input forces may be caused by operative movements of the support on the partial arm relative to the harness on the body. The force amplifier may be rotatable relative to the support during the operative movements to maintain a generally linear alignment between the input member and the force amplifier. The force transfer elements may be operable with the output forces to cause a first portion of the plurality of digits to move toward the hand body faster than a second portion of the plurality of digits.

The partial arm may comprise an elbow and the support may be wearable on a proximal portion of the partial arm located above the elbow, such that the adjustable elbow apparatus is not required.

Alternatively, the partial arm may comprise a partial humerus bone and may not comprise an elbow, in which case the support may comprise the adjustable elbow apparatus. The elbow apparatus may comprise structures defining: an upper arm prosthetic wearable on a proximal portion of the partial arm located adjacent the partial humerus bone; a first elbow portion fixedly engageable with the upper arm prosthetic; and a second elbow portion that is rotatably engageable with the first elbow portion and fixedly engageable with the terminal unit apparatus, wherein the force amplifier is rotatably engaged with upper arm prosthetic.

Any structures described herein may be 3D printable and/or otherwise formable.

Related apparatus and systems also are expressly or inherently described, along with various kits and methods related thereto.

BRIEF DESCRIPTION OF THE DRAWINGS

The accompanying drawings, which are incorporated in and constitute part of this disclosure, illustrate exemplary aspects that, together with the written descriptions, serve to explain the principles of this disclosure. Numerous aspects are particularly described, pointed out, and taught in the written descriptions. Some structural and operational aspects may be even better understood by referencing the written portions together with the accompanying drawings, of which.

DETAILED DESCRIPTION

Figure 1:
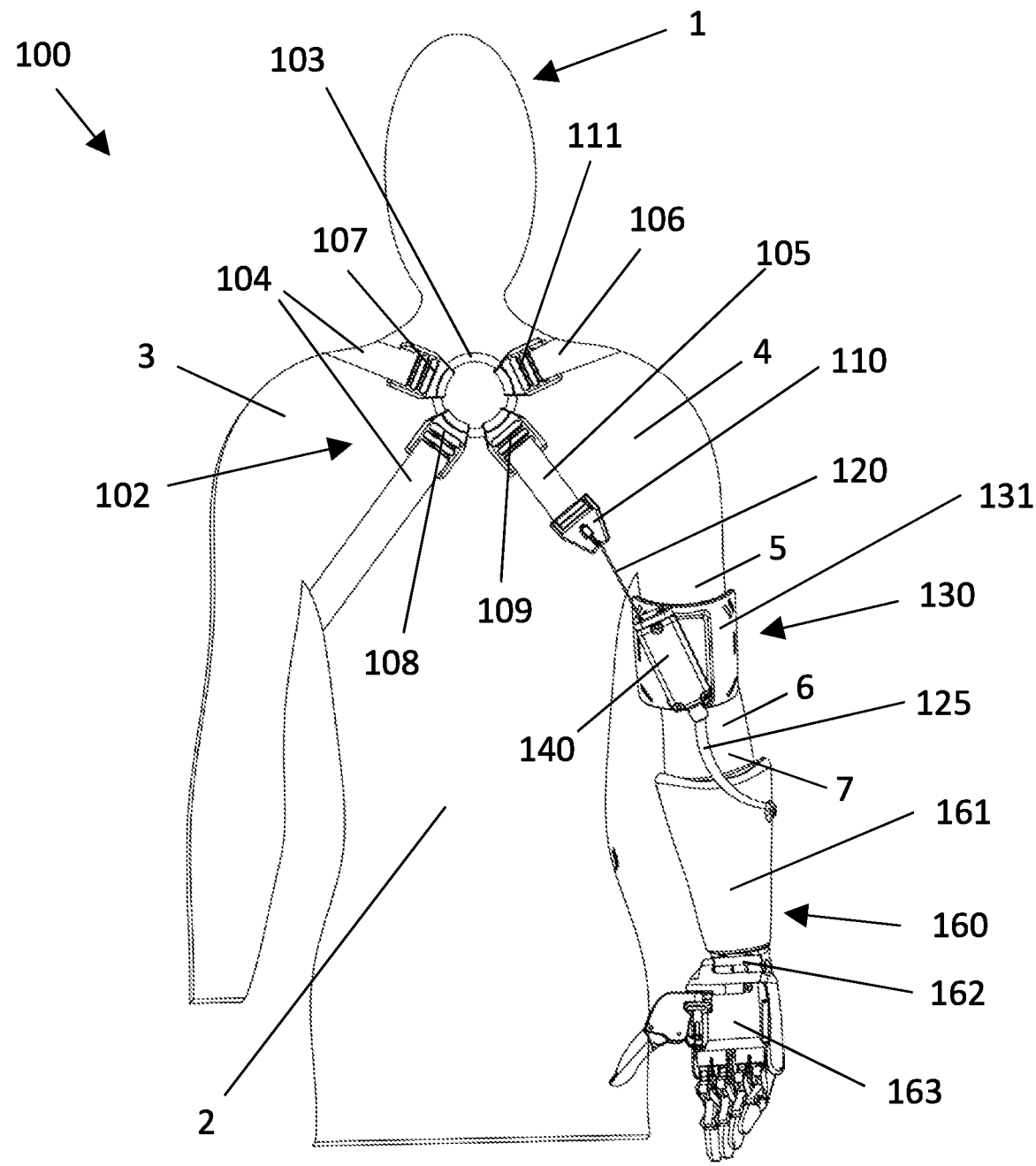
FIG. 1 depicts a back view of an exemplary upper arm prosthetic system comprising a force amplification apparatus and a terminal unit apparatus.

Aspects of the present disclosure are not limited to the exemplary structural details and component arrangements described in this description and shown in the accompanying drawings. Many aspects of this disclosure may be applicable to other aspects and/or capable of being practiced or carried out in various variants of use, including the examples described herein.

Throughout the written descriptions, specific details are set forth in order to provide a more thorough understanding to persons of ordinary skill in the art. For convenience and ease of description, some well-known elements may be described conceptually to avoid unnecessarily obscuring the focus of this disclosure. In this regard, the written descriptions and accompanying drawings should be interpreted as illustrative rather than restrictive, enabling rather than limiting.

Exemplary aspects of this disclosure reference various upper arm prosthetic apparatus and systems. Some aspects are described with reference to a particular type of prosthetic (e.g., a hand or elbow) operable by a particular user (e.g., children or smaller humans) with a particular power source (e.g., body powered) to perform a particular function (e.g., grasping). Unless claimed, these exemplary aspects are provided for convenience and not intended to limit this disclosure. Accordingly, the concepts described in this disclosure may be utilized with any type of prosthetic operable by any user with any power source to perform any function, including the particular aspects described herein.

Several reference axes are described, including: a longitudinal axis X-X and a lateral axis Y-Y. Some aspects are described relative to these axes. Each longitudinal axis X-X and Y-Y may define relative arrangements of one element to another. For example, each longitudinal axis X-X may be non-parallel with at least one lateral axis Y-Y in some perspectives, meaning that axis Y-Y may extend across and/or intersect axis X-X. The term "elongated" may describe any aspect having a length along one of axes X-X or Y-Y that is longer in relation to a width along a non-parallel one of axes X-X or Y-Y. Additional reference axes, movements, and forces also may be described. These relative terms are provided for convenience and do not limit this disclosure unless claimed.

Anatomical terms such as "proximal" and "distal" are used to orient some aspects relative to a human body. Proximal generally refers to directions and/or positions closer to the body along a reference axis and distal generally refers to directions and/or positions away from the body along the reference axis. As shown in the drawings, proximal directions may be generally indicated on the reference axis by a directional arrow "P" and distal directions may be generally indicated on the axis by a directional arrow "D." Similar to above, these anatomical terms are provided for convenience and do not limit this disclosure unless claimed.

As used herein, inclusive terms such as "comprises," "comprising," "includes," "including," and variations thereof, are intended to cover a non-exclusive inclusion, such that any pole apparatus, method, system, or element thereof comprising a list of elements does not include only those elements, but may include other elements not expressly listed and/or inherent thereto. Unless stated otherwise, the term "exemplary" is used in the sense of "example," rather than "ideal." Various terms of approximation may be used in this disclosure, including "approximately" and "generally." Approximately means "roughly" or within 10% of a stated number or outcome. Generally means "usually" or more than a 50% probability.

Terms such as "engageable with," "engaged with," and "engaging" are used in this disclosure to describe a connection between two or more elements. Some connections may be "fixedly engageable" and thus non-rotatable, as when the two or more elements are formed together and cannot be rotated independently without damage. Other connections may be "rotatably engageable," as when the two or more elements are coupled together by attachment elements (e.g., pins, screws, etc.) and/or structural elements (e.g., joints, hinges, etc.) allowing for independent rotation. Terms such as "movably engageable" or "slidably engageable" may be similarly used to describe some connections. The term "pin" is often used as an exemplary attachment element and should be broadly interpreted to include any type of rotation-enabling structure. Accordingly, unless stated otherwise, the term engageable and its equivalents may comprise any such variations.

Figure 2:
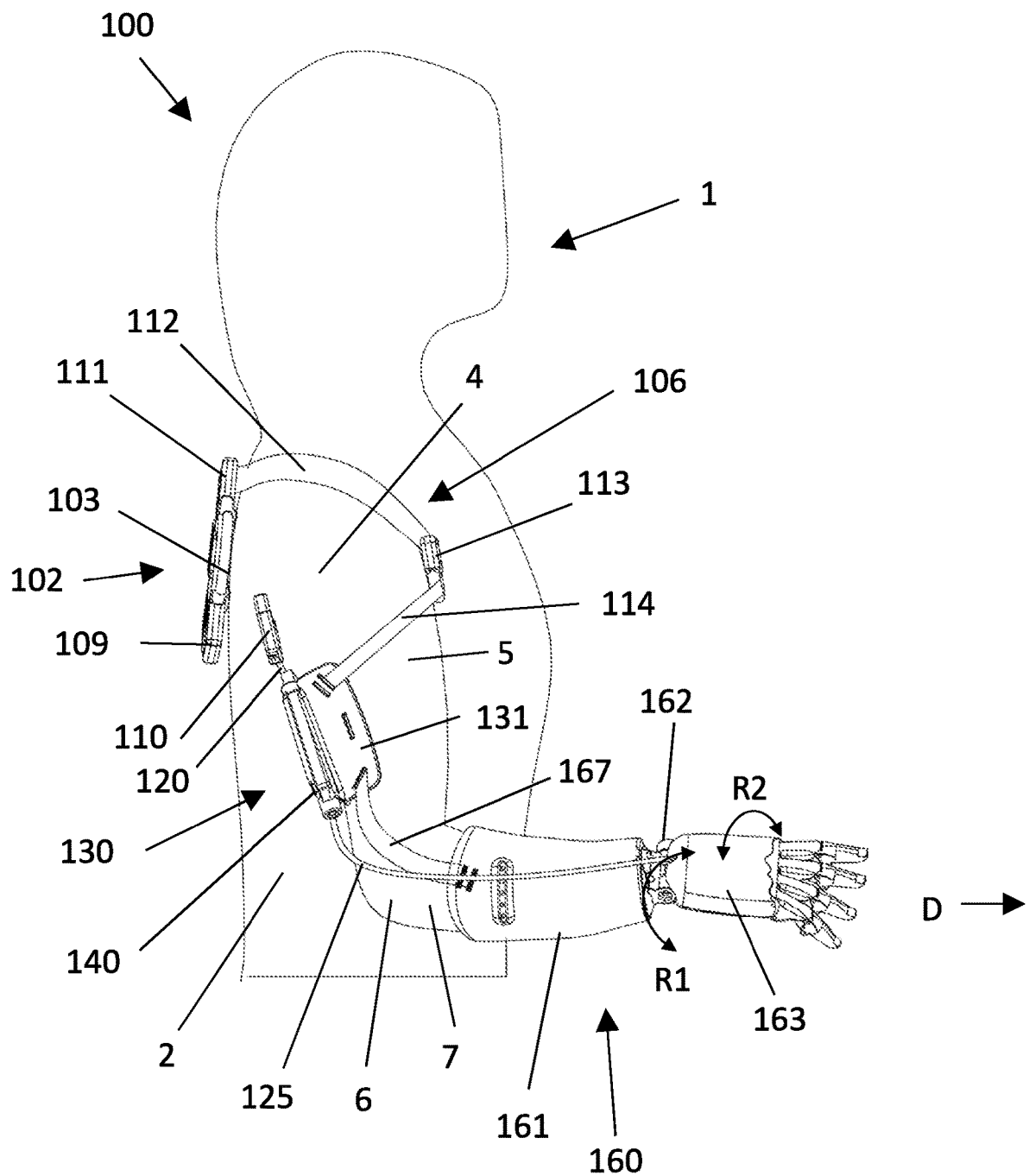
FIG. 2 depicts a side view of the FIG. 1 system.

Aspects of this disclosure are now described with reference to an exemplary upper arm prosthetic system 100 for a human subject 1 having a body 2 comprising a full arm 3 and a partial arm 4. As shown in FIGS. 1 and 2, partial arm 4 may comprise a proximal portion 5, an elbow 6, and a distal portion 7; and system 100 may comprise any combination of: (i) a harness 102; (ii) an input member 120; (iii) a force amplification apparatus 130; (iv) an output member 125; and/or (iv) a terminal unit apparatus 160. As now described, harness 102 may transfer input forces to input member 120; force amplification apparatus 130 may receive the input forces from input member 120, convert the input forces into output forces, and transfer the output forces to output member 125; and terminal unit apparatus 160 may be operable with the output forces to grasp an object.

Harness 102 may be wearable on body 2. For example, harness 102 may comprise a traditional "figure 8" style harness that has been modified for use in system 100. As shown in FIG. 1, harness 102 may comprise a central attachment 103, a shoulder strap 104, an input member strap 105, and a support strap 106. Shoulder strap 104 may comprise a clip 107 engageable with central attachment 103, a clip 108 engageable with central attachment 103, and length between clips 107 and 108 that is sized to wrap around any portion of body 2 (e.g., around a shoulder of full arm 3). Input member strap 105 may comprise a clip 109 engageable with central attachment 103, a clip 110 engageable with input member 120, and length extending between clips 109 and 110. As shown in FIGS. 1 and 2, support strap 106 may comprise a clip 111 engageable with central attachment 103, a first length 112 extending between clip 111 and a bidirectional clip 113, a second length 114 extending between clip 113 and apparatus 130.

Figure 3:
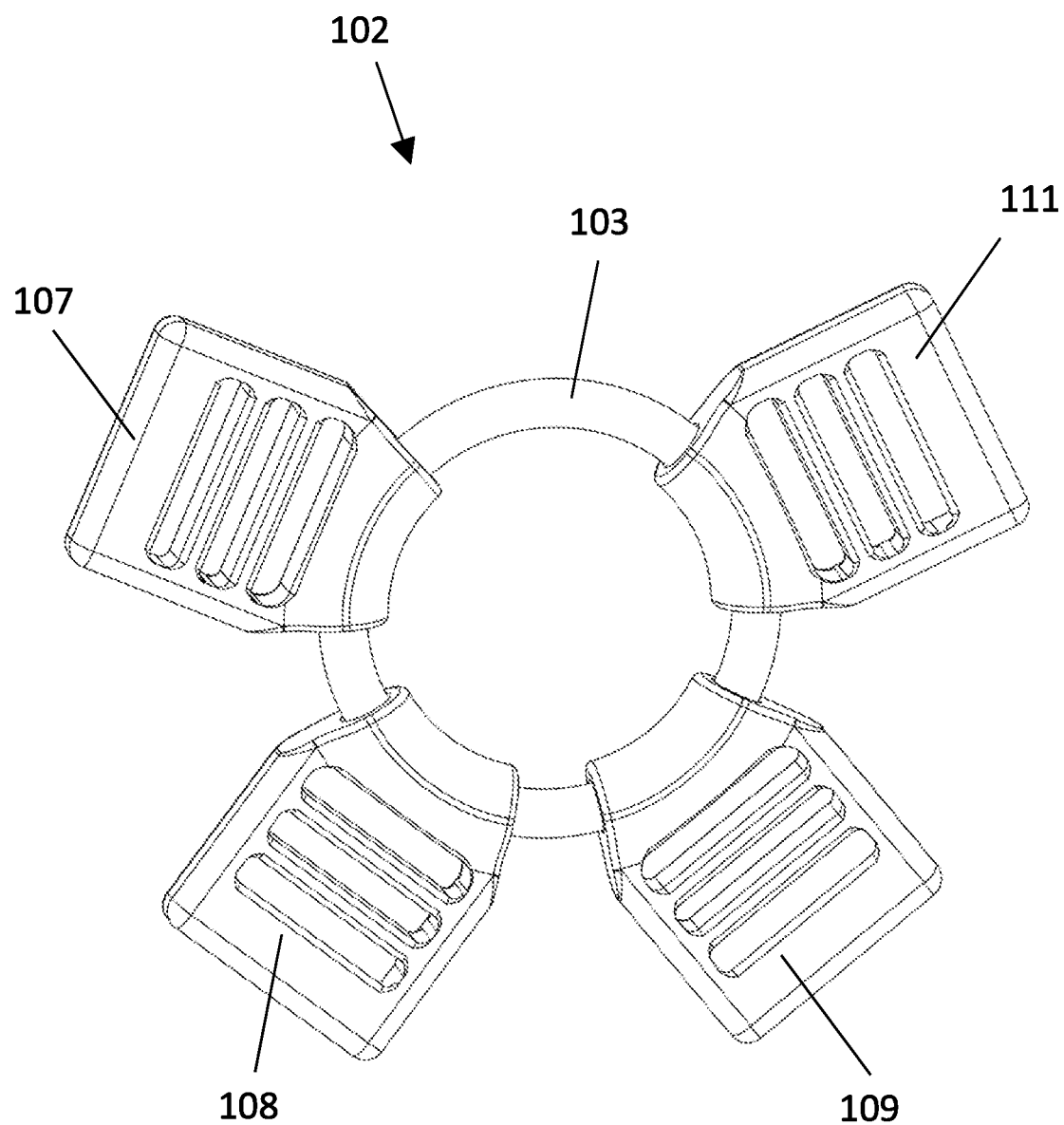
FIG. 3 depicts an exemplary central attachment for the FIG. 1 system.

As shown in FIG. 3, central attachment 103 may comprise a structure defining a generally circular ring. Clips 107, 108, 109, and/or 111 may be slidably engageable with the generally circular ring so that a fit of harness 102 is continuously adjustable relative to body 2. A structure of each clip 107, 108, 109, and 111 may define a first end engageable with central attachment 103 and a second engageable with a corresponding one of straps 104, 105, or 106. Each first end may define one or more openings and/or bars engageable with an end of strap 104, 105, or 106. Each second end may define a generally circular channel that is sized receive a portion of the generally circular ring and resiliently expandable.

Figure 4:
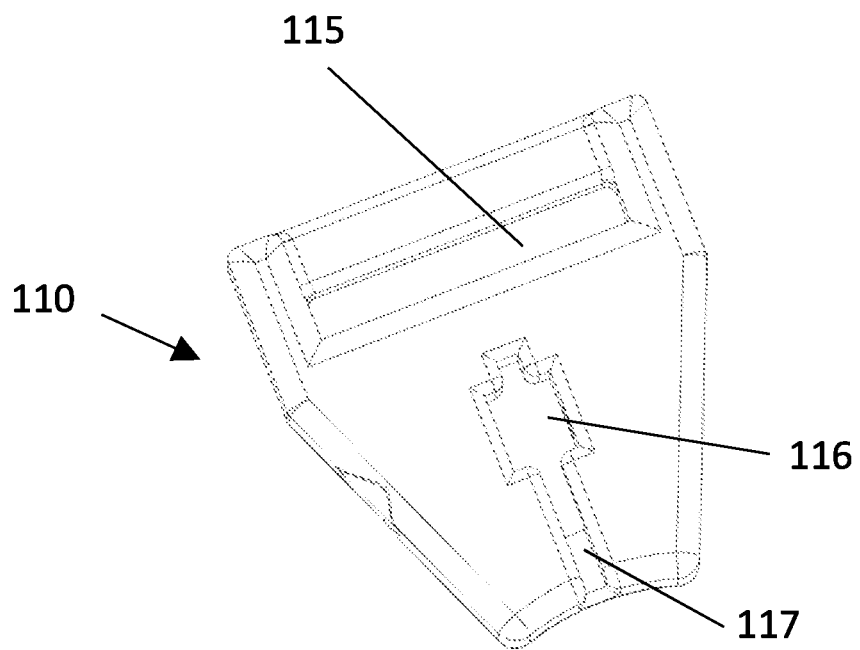
FIG. 4 depicts an exemplary clip for the FIG. 1 system.
Figure 5:
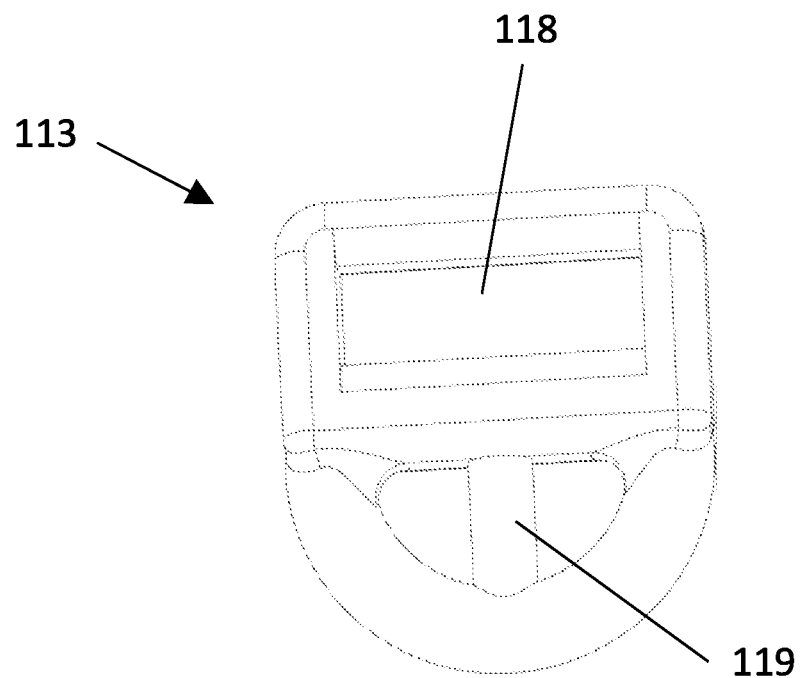
FIG. 5 depicts an exemplary another exemplary clip for the FIG. 1 system.

As shown in FIG. 4, the structure of clip 110 may define a first end engageable with input member strap 105 and a second end engageable with input member 120. The first end may define one or more openings and/or bars 115 engageable with input member strap 105. The second end may define a catchment opening 116 and/or a channel 117 engageable with an end of input member 120. As shown in FIG. 5, the structure of bi-directional clip 113 may define a first end engageable with length 112 of support member strap 106 and a second end engageable with length 114 of strap 106. Here, the first end may comprise one or more openings and/or bars 118 engageable with length 112 and the second end may similarly comprise one or more openings and/or bars 119 engageable with clip 113.

Input member 120 and output member 125 may comprise any type of elongated actuating member, including flexible elements such as cable or wires, and comparatively rigid elements such as beams, rods, or shafts. As shown in FIGS. 1 and 2, input member 120 may comprise a flexible cable that is routable between clip 110 and force amplification apparatus 130 along a generally linear path extending therebetween. As also shown in FIGS. 1 and 2, output member 125 may be a Bowden cable comprising a flexible cable and a sheath, in which the cable and the sheath are routable between force amplification apparatus 130 and terminal unit apparatus 160 along any path therebetween, and the cable is movable relative to sheath.

Figure 6:
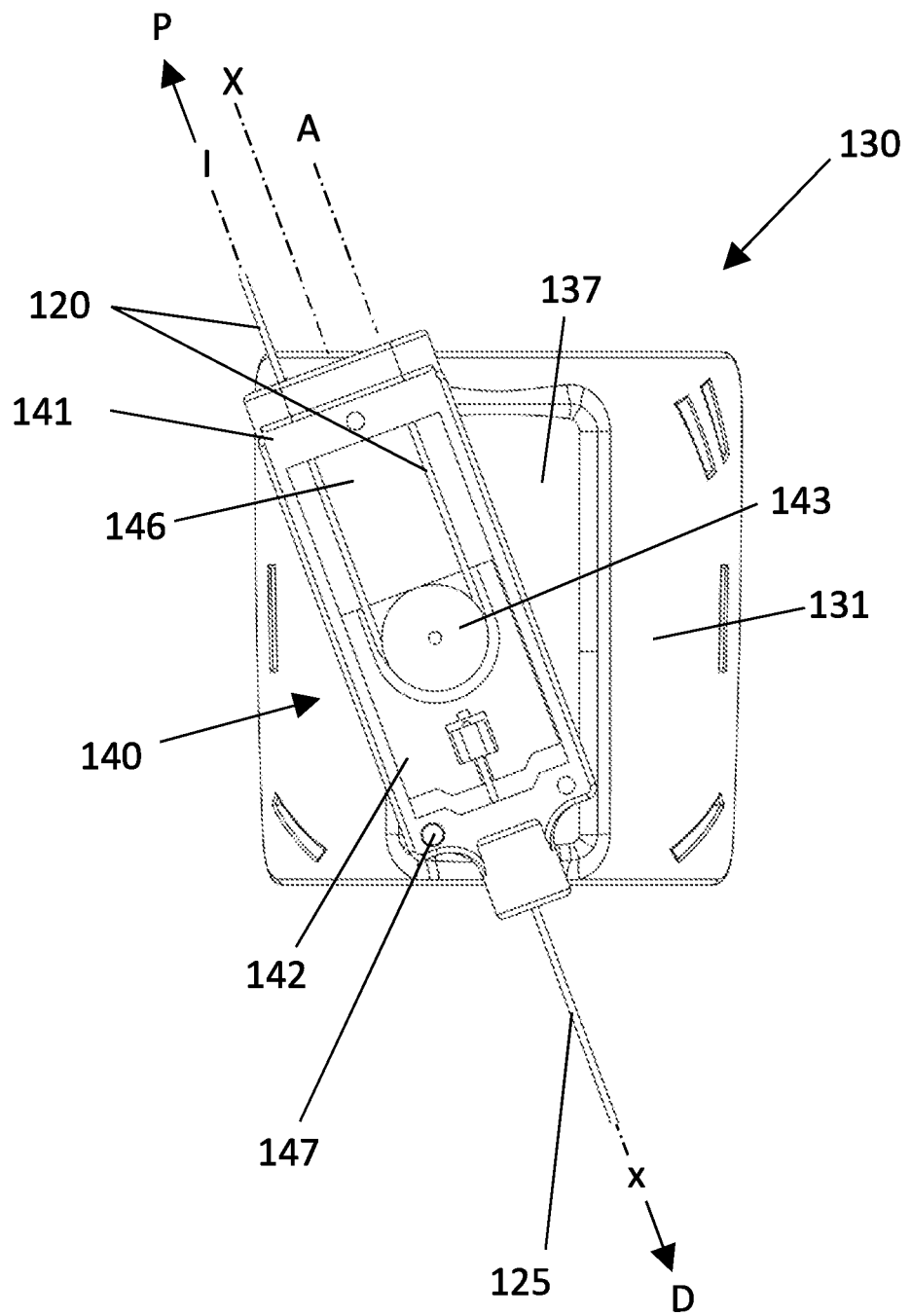
FIG. 6 depicts an exemplary force amplification apparatus in a first operating position.
Figure 8:
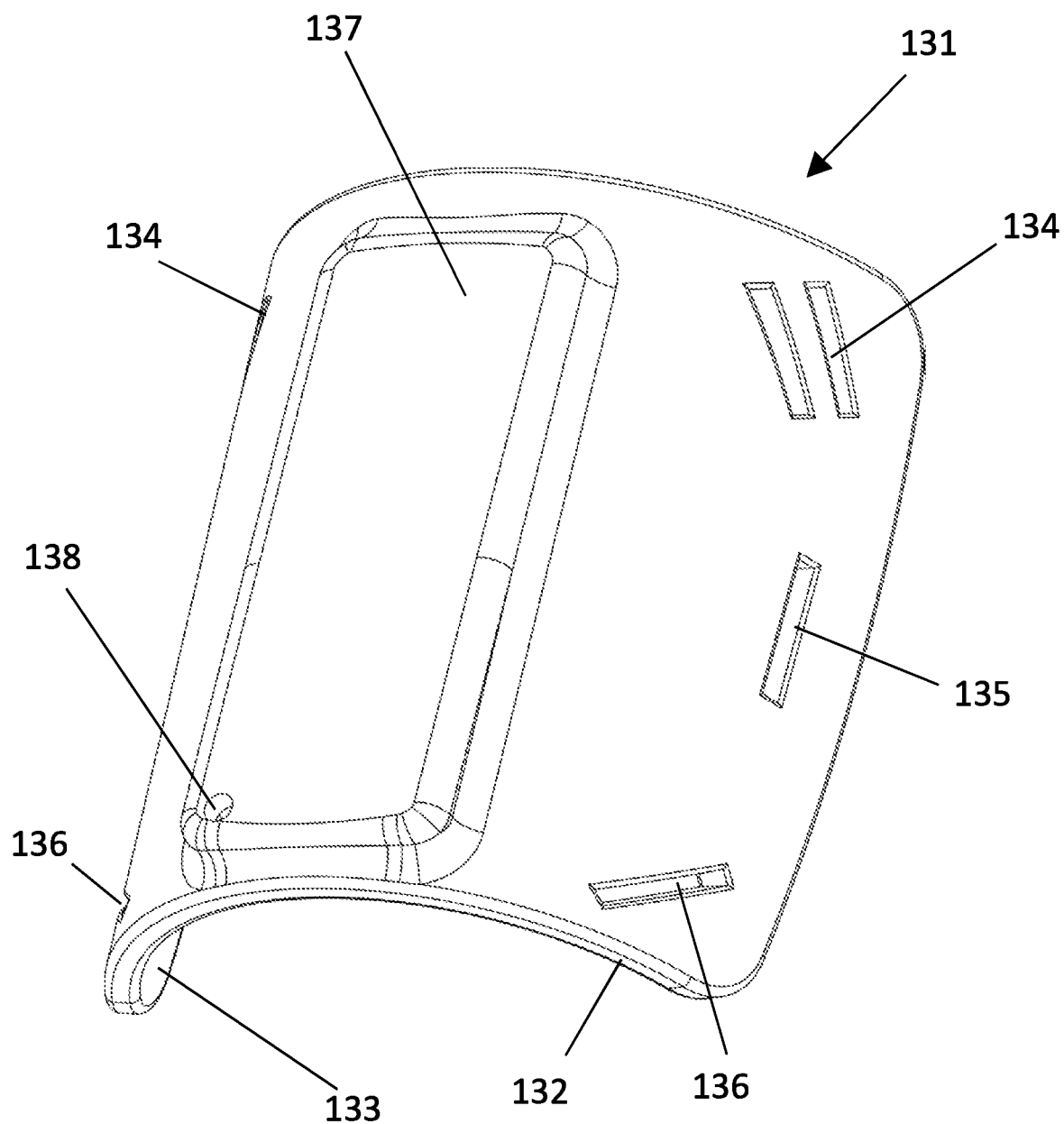
FIG. 8 depicts an exemplary support for the FIG. 6 apparatus.

As shown in FIG. 6, force amplification apparatus 130 may comprise a support 131 and a force amplifier 140 rotatably engageable with support 131. As shown in FIG. 8, support 131 may comprise a structure defining a semicircular cross-sectional area 132 extending along a longitudinal axis X-X, a skin-facing surface 133 engageable with exterior surfaces of proximal portion 5 of partial arm 4, proximal openings 134, interior openings 135, distal openings 136, and a raised platform 137, and a passage 138. Skin-facing surface 133 may be contoured for placement against triceps muscles of proximal portion 5 of partial arm 4. Proximal openings 134 may be engageable with length 114 of strap 106 to maintain a position of skin-facing surface 133 against portion 5. For example, strap 106 may be routed through proximal openings 134 and openings and/or bars 119 of bi-directional clip 113 and to encircle proximal portion 5 of arm 4; and then tensioned between openings 134 and openings and/or bars 119 to maintain the position of surface 133. Additional straps may be similarly used with openings 135 and 136 for the same reason.

Within system 100, force amplifier 140 may receive the input forces from input member 120 by any means and utilize any type of mechanical advantage to convert the input forces into the output forces. Any type of simple machine may be used to impart the mechanical advantage, including a block-and-tackle, a lever, a pulley, and the like. As shown in FIG. 6, for example, force amplifier 140 may comprise a slider base 141, a slider 142, and a pulley 143. As now described, force amplifier 140 may utilize pulley 143 to impart a mechanical advantage that amplifies (i.e., increases) the input force into the output force, allowing human subject 1 to operate terminal unit apparatus 160 even if they are smaller in stature and otherwise unable to generate a sufficient amount of force.

Figure 9:
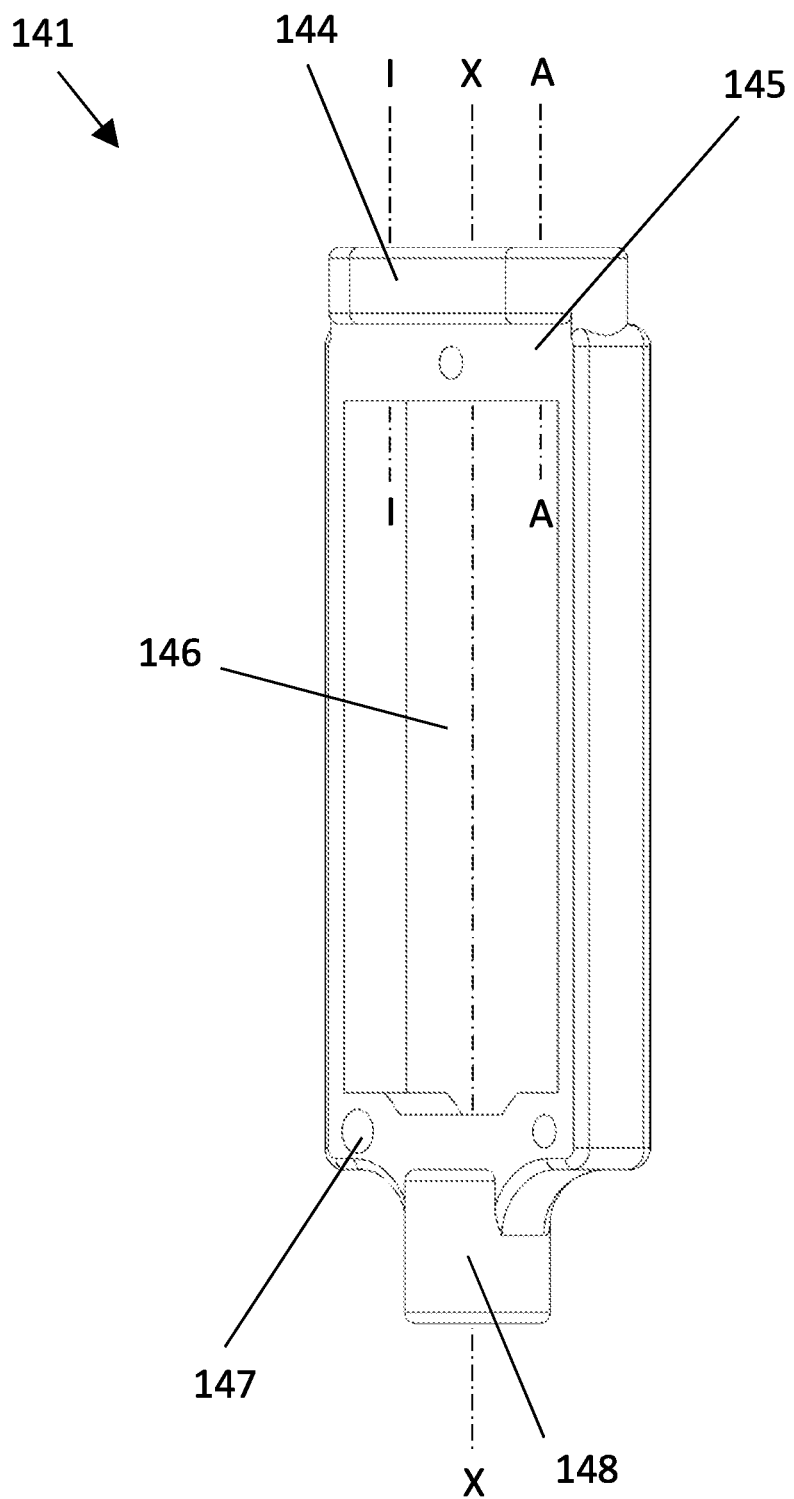
FIG. 9 depicts an exemplary slider base for the FIG. 6 apparatus.

As shown in FIG. 9, slider base 141 may comprise a structure extending a longitudinal axis X-X to define an inlet 144, an input member attachment portion 145, an interior cavity 146, a support attachment opening 147, and an outlet 148. Inlet 144 may be located at a distal end of base 141 and comprise a passage configured to guide input member 120 into interior cavity 146 toward pulley 143. As shown, inlet 144 may extend along an input axis I-I and input member attachment portion 145 may extend along an attachment axis A-A, both of which may be general parallel to and offset from axis X-X. Input member attachment portion 145 may comprise structures that are engageable with an end of input member 120 from within cavity 146, including structures similar to catchment opening 116 and/or channel 117 of clip 110 (or any other structures for crimping or otherwise engaging the end of input member 120). Interior cavity 146 may comprise side walls and/or end walls defining a movement path for slider 142. As also shown in FIG. 9, the side walls may extend along longitudinal axis X-X and be slidably engageable with slider 142, allowing it to be slid back and forth within cavity 146. One end wall of interior cavity 146 may interlock with a corresponding surface of slider 142 to resist lateral forces. Outlet 148 may comprise a passage configured to guide output member 125 into cavity 146 toward slider 142 along axis X-X. In some aspects, a sheath of member 125 may be engageable with outlet 148.

Force amplifier 140 may be rotatable relative to support 131 in order to increase the reliability of system 100 by limiting or preventing any unwanted flexure of input member 120 that might otherwise cause some portion of the input forces to be lost. In some aspects, force amplifier 140 may be rotatable relative to support 131 during operative movements of partial arm 4 relative to body 2 in order to maintain a generally linear alignment between input member 120 and force amplifier 140. As shown in FIG. 6, passage 138 of support 131 may extend through raised platform 137 and cross-section 132 so that force amplifier 140 may be rotatable engaged with raised platform 137 by inserting a pin through opening 147 and passage 138. Raised platform 137 may be offset from the environment-facing surface by a distance that permits force amplifier 140 to rotate freely relative to support 131.

Figure 10:
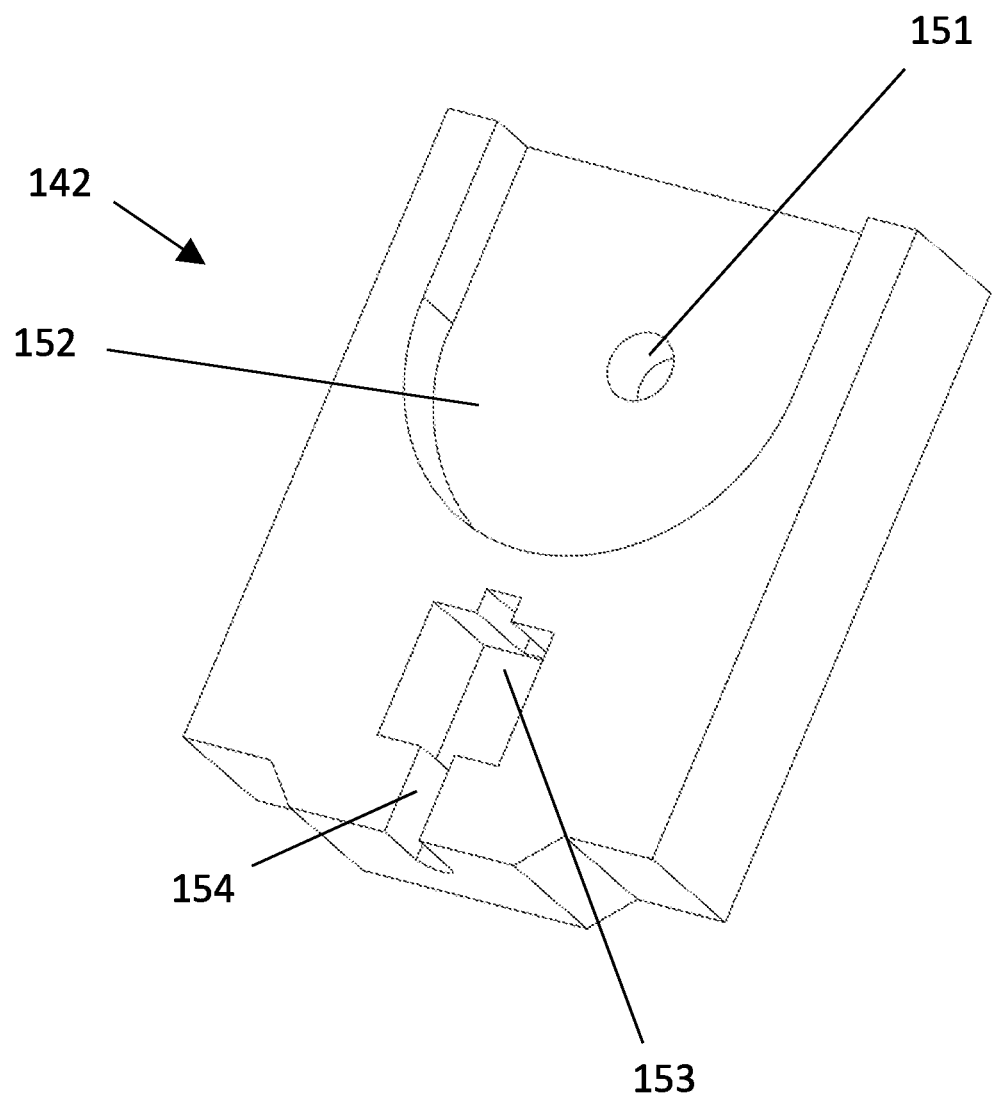
FIG. 10 depicts an exemplary slider for the FIG. 6 apparatus.
Figure 11:
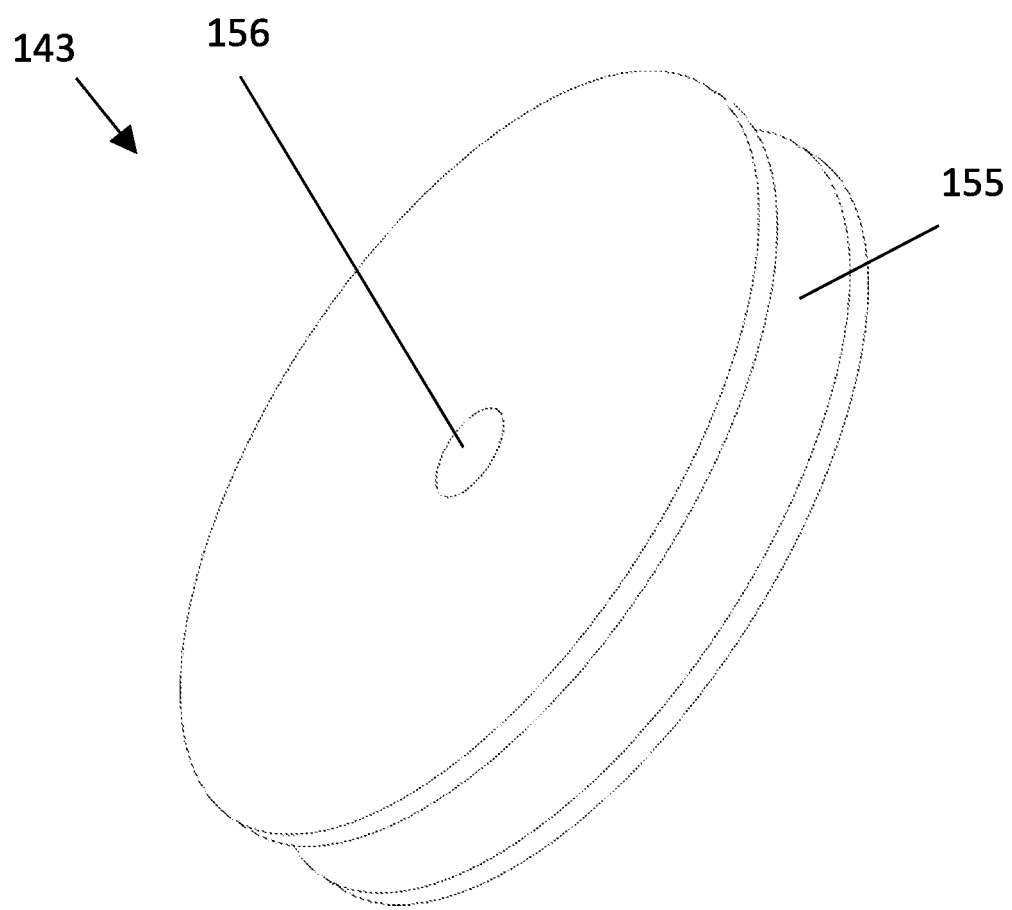
FIG. 11 depicts an exemplary pulley for the FIG. 6 apparatus.

As shown in FIG. 10, slider 142 may comprise a structure defining an opening 151, a rotational cavity 152, exterior surfaces engageable with the sidewalls of interior cavity 146 to permit sliding of slider 142 along longitudinal axis X-X within interior cavity 146, a catchment opening 153, and a channel 154. Opening 151 may extend through slider 142. Rotational cavity 152 may be open at one end and sized to receive pulley 143 and input member 120. Catchment opening 153 and channel 154 may be engageable with an end of output member 125. As shown in FIG. 11, pulley 143 may comprise a structure defining an annular channel 155 and an opening 156. Annular channel 155 may be configured to receive a portion of input member 120 therein. Opening 156 may extend through pulley 143.

Exemplary methods of assembling force amplification apparatus 130 are now described with reference to an assembly method 300. For example, method 300 may comprise one or more of: (i) rotatably engaging pulley 143 with slider 142 (a step 310); (ii) slidably engaging slider 142 with slider base 141 (a step 320); (iii) rotatably engaging slider base 141 with support 131 (a step 330); (iv) fixedly engaging input member 120 with pulley 143 and slider base 141 (a step 340); and/or (v) fixedly engaging output member 125 with slider 142 (a step 350).

According to FIG. 6, step 310 may comprise locating pulley 143 in rotational cavity 152 and engaging a pin with opening 151 and opening 156 so that pulley 143 is rotatably engaged with slider 142 in cavity 152. Step 320 may comprise locating slider 142 and pulley 143 in interior cavity 146 so that each of slider 142, pulley 143, and the pin are generally aligned with a longitudinal axis X-X (e.g., as shown in FIG. 9), allowing slider 142 and pulley 143 to move linearly along axis X-X while pulley 143 rotates relative to slider 142 in cavity 152. As further shown in FIG. 6, step 330 may comprise engaging a pin with opening 147 of slider base 141 and passage 138 of support 131 so that slider base 141 is rotatable relative to support 131 to prevent unwanted flexure of input member 120.

Step 340 may comprise routing an end of input member 120 through inlet 144 along input axis I-I, receiving a portion of member 120 in annular channel 155, and engaging the end of member 120 with the input member attachment portion 145 along an attachment axis A-A. Step 350 may comprise routing an end of output member 125 through outlet 148 along longitudinal axis X-X; and receiving that end in catchment opening 153 and channel 154 of slider 142 so that output member 125 is generally aligned with axis X-X. Method 300 may further comprise sealing interior cavity 146 to maintain the various engagements contained therein. As shown in FIG. 1, method 300 may comprise attaching a cover to slider base 141 at various locations using adhesives, interlocking structures, or screws.

Once force amplification apparatus 130 has been assembled according to method 300, then it may be utilized to receive input forces from input member 120, amplify the input forces into the output forces, and transfer the output forces to output member 125. The input forces may be generated by moving harness 102 relative to force amplification apparatus 130. For example, when harness 102 is worn on body 2 and support 131 is worn on proximal portion 5 of partial arm 4, then the input forces may be caused by operative movements of proximal portion 5 and support 131 engaged therewith relative to body 2 and harness 102 engaged therewith. As shown in FIG. 2, the operative movements may comprise moving proximal portion 5 away from body 2 in a distal direction D until input member 120 is tensioned between clip 110 and force amplification apparatus 130. Because the length of input member 120 between clip 110 and slider 142 is fixed and the position of harness 102 is relative to body 2 is generally fixed, the input forces may be caused by any further movement of portion 5 in direction D.

Figure 7:
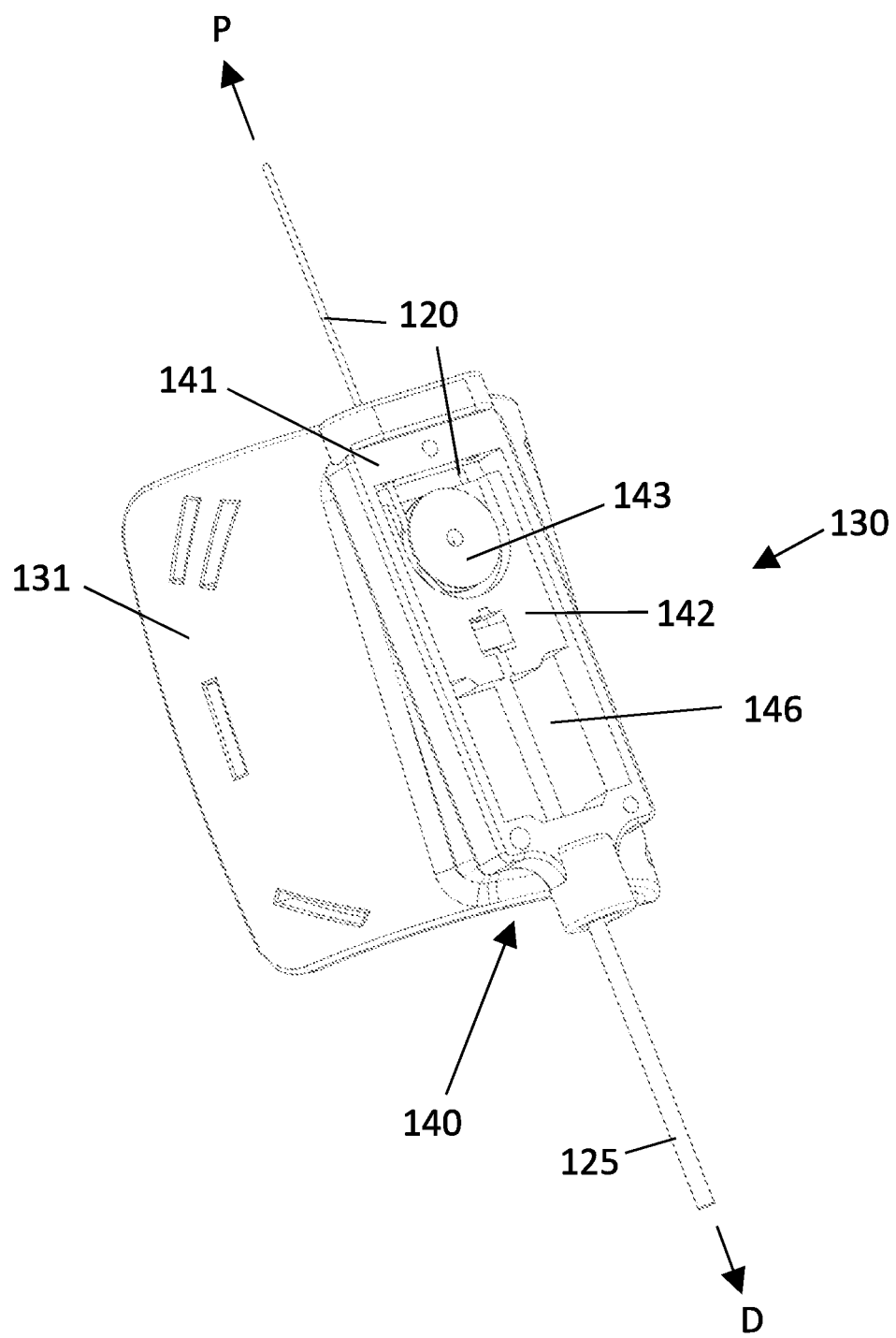
FIG. 7 depicts the FIG. 6 apparatus in a second operation position.

As shown in FIG. 6, the input forces may act on input member 120 in a proximal direction P when proximal portion 5 is moved in distal direction D. As shown in FIG. 7, because input member 120 is routed through annular channel 155 of pulley 143 and engaged with (e.g., crimped onto) slider base 141, the input forces applied to member 120 may act against slider base 141 and pulley 143 to pull slider 142 proximally when slider base 141 is moved distally. In particular, the input forces may be applied to input member 120 along input axis I-I and then transferred to slider 142 along longitudinal axis X-X so that a distance between axes I-I and A-A (e.g., a distance relative to a diameter of pulley 143) may cause a mechanical advantage that amplifies the input force into the output force. Because it is also engaged with output member 125, slider 142 also may transfer the output force to output member 125 for use by terminal unit apparatus 160. A magnitude of the mechanical advantage may be adjusted to match the strength of body 2 and/or partial arm 4 with a minimum actuating force of terminal unit apparatus 160. For example, the diameter of pulley 143 and thus a distance between axis I-I and A-A may be configured such that the output force is equal to at least two times the input force (or 200% of the input force), making it considerably easier for a smaller or weaker body 2 and/or partial arm 4 to utilize terminal unit apparatus 160 within system 100.

Other aspects of force amplification apparatus 130 also may be configured to maximize the mechanical advantage applied therewith. For example, the input forces may be most effectively generated when a line of action for input member 120 between harness 102 and force amplification apparatus 130 extends along a generally linear path that avoids losses caused by friction with proximal portion 5 of arm 4 and/or excessive curvature of input member 120. As described above, force amplifier 140 may be rotatable relative to support 131 to continuously avoid these losses by dynamically maintaining the generally linear path during a wide variety of operating movements between body 2 and proximal portion 5, including any upward, downward, and side-to-side movements that might be performed to grasp an object at different locations relative to body 2 and a range of motion for arm 4.

Terminal unit apparatus 160 may be engageable with output member 125 and operable with the output forces to grasp an object. As shown in FIGS. 1 and 2, terminal unit apparatus 160 may comprise a socket 161, a wrist 162, and a prosthetic hand 163. As now described, prosthetic hand 163 may comprise force transfer elements operable with the output forces to open and close finger digits 164 in a more human-like manner.

Figure 12:
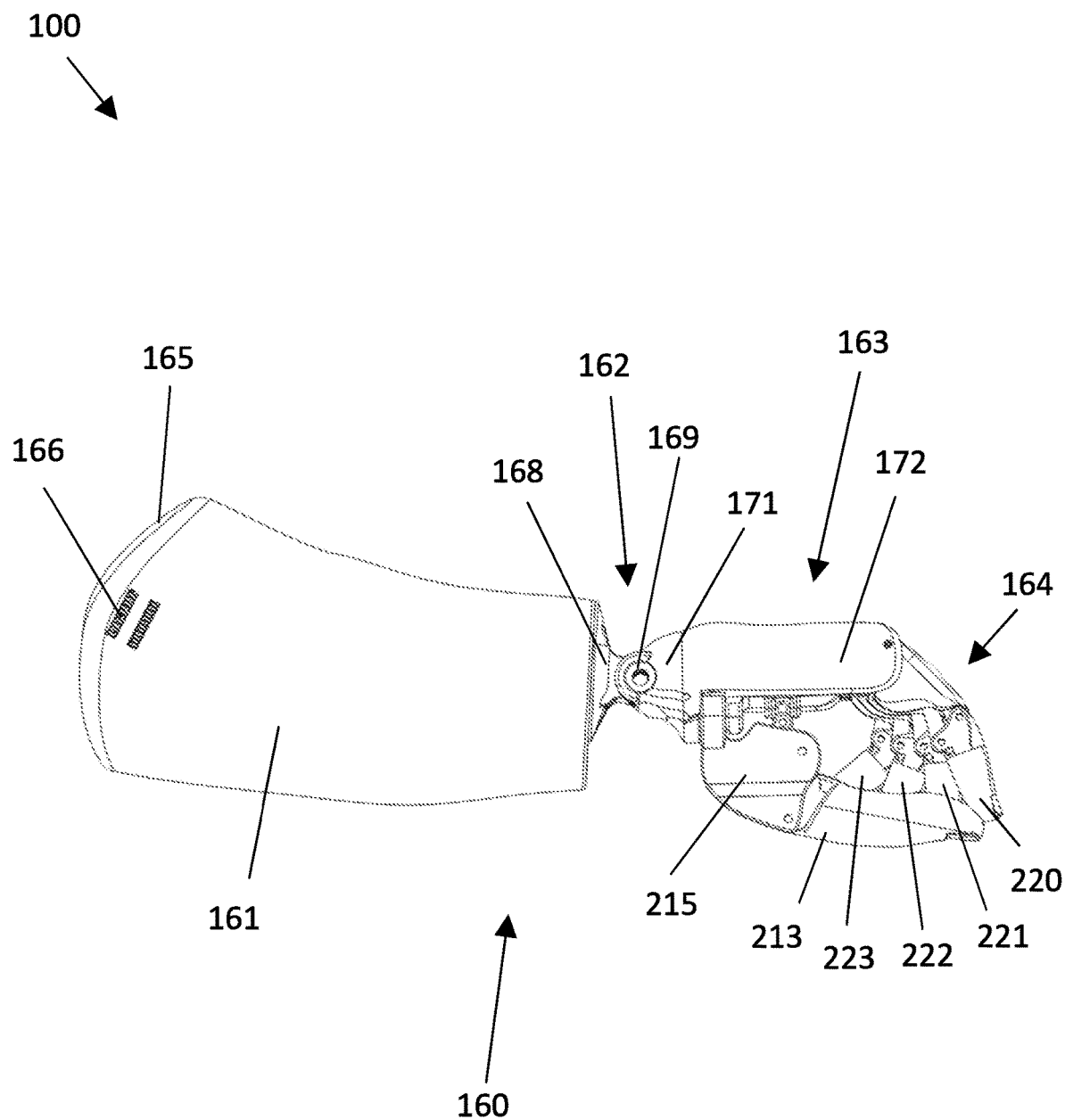
FIG. 12 depicts an exemplary terminal unit apparatus for the FIG. 1 system comprising a socket and an exemplary prosthetic hand.

Socket 161 may be configured to receive distal portion 7 of partial arm 4. As shown in FIG. 12, socket 161 may comprise a structure defining an interior cavity 165 and proximal openings 166. Interior cavity 165 may be configured to receive distal portion 7. For example, exterior surfaces of distal portion 7 may be approximated or scanned to create an anatomical data set, and interior cavity 165 may be formed or printed based on the anatomical data set to obtain a more precise fit with portion 7.

As shown in FIG. 2, a strap 167 may extend between openings 136 of support 131 and openings 166 of socket 161 to help maintain a position of socket 161 relative to distal portion 7.

As shown in FIG. 12, wrist 162 may comprise structures defining a proximal hinge portion 168 and a distal hinge portion 169. Proximal hinge portion 168 may be rotatably engageable with distal hinge portion 169 so that hand 163 is rotatable about at least one axis relative to distal portion 7, much like a human wrist. As shown in FIG. 2, hinge portions 168 and 169 may permit rotation of hand 163 relative to socket 161 in a first rotational direction R1. Proximal hinge portion 168 also may be rotatably engaged with a distal end of socket 161. For example, hinge portion 168 may be rotatably engageable with the distal end of socket 161 so that hand 163 is relative to socket 161 in a second rotational direction R2.

Figure 13:
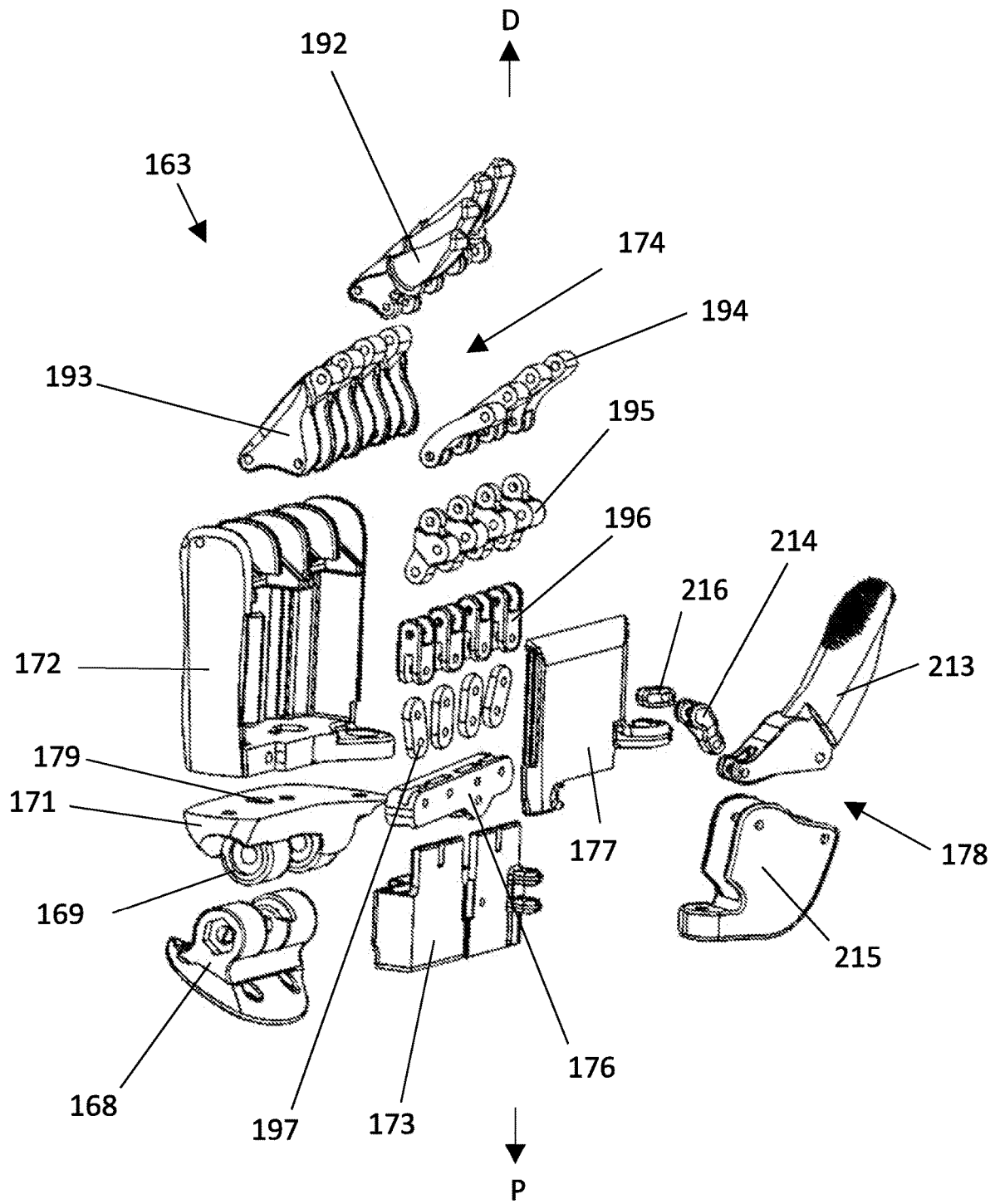
FIG. 13 depicts an exploded view of the FIG. 12 hand.

As shown in FIG. 13, prosthetic hand 163 may comprise a base 171 and a hand body 172. Base 171 may be integral with distal hinge portion 169 and configured to provide an operating platform for prosthetic hand 163. As shown, base 171 may comprise an irregular shaped solid structure that defines hinge portion 169, a channel 179 extending through base 171 to receive output member 125, and various attachment openings. Hand body 172 may be fixedly engageable with base 171 and the force transfer elements of hand 163 may be operatively contained in hand body 172, such that base 171 provides a reaction surface for the force transfer elements. As now described, for example, the force transfer elements may of prosthetic hand 163 may comprise a slide frame 173, a finger digit assembly 174, a rocker 176, a cover 177, and a thumb digit assembly 178.

Figure 14:
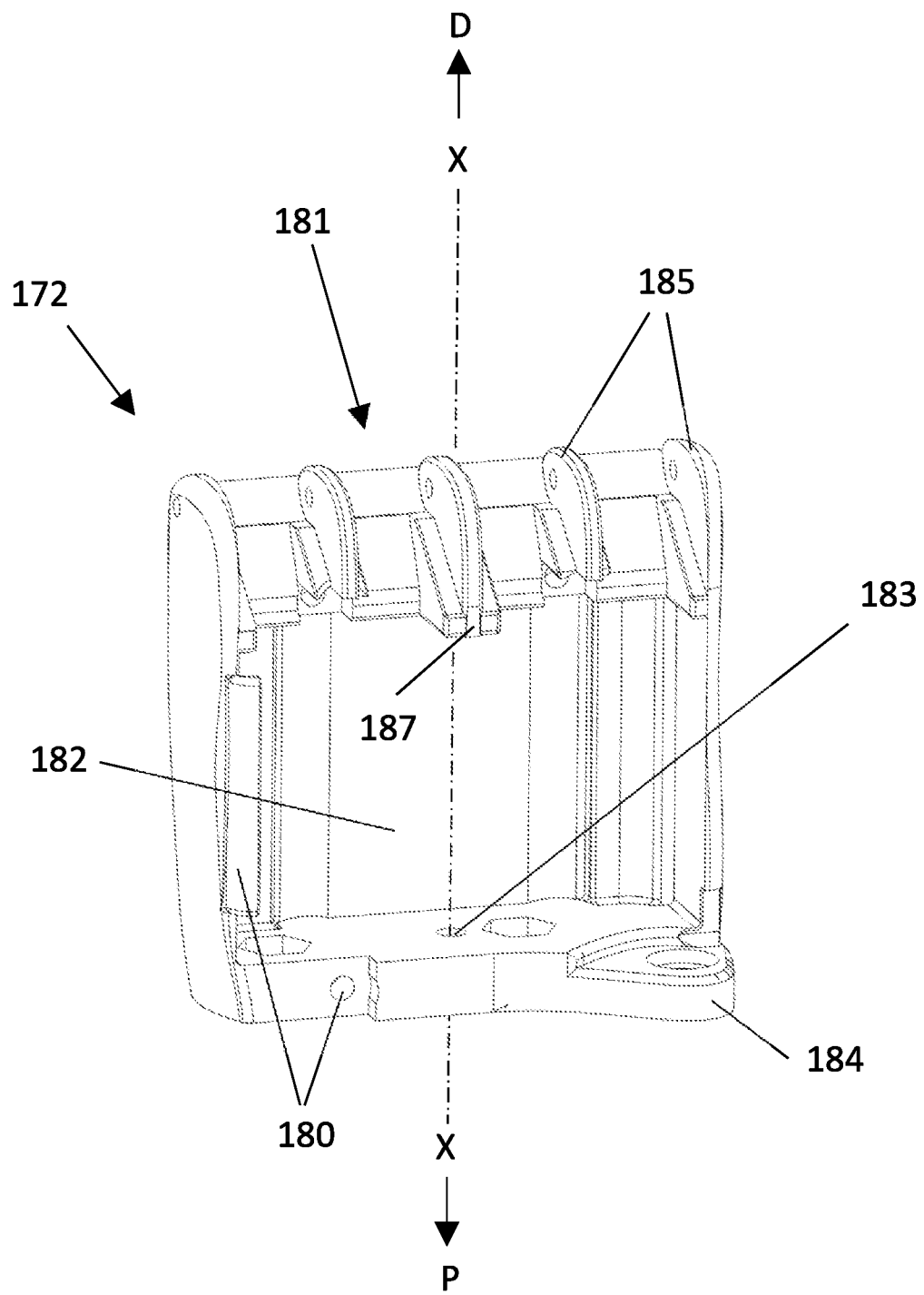
FIG. 14 depicts an exemplary hand body for the FIG. 12 hand.

As shown in FIG. 14, hand body 172 may comprise a structure defining cover securing elements 180, finger digit portions 181, an interior cavity 182, a channel 183, and a thumb hinge base 184. The structure of hand body 172 may extend along a longitudinal axis X-X that defines proximal and distal directions relative to base 171. Cover securing elements 180 may comprise an elongated hinge portion (e.g., extending along axis X-X) and one or more openings. Each finger digit portion 181 may comprise opposing supports 185 engageable with finger digit assembly 174. As shown in FIG. 14, opposing supports 185 may be spaced apart along an axis that is non-parallel with longitudinal axis X-X, and each support 185 may comprise a passage extending there through along that axis. Interior cavity 182 may comprise side walls and end walls defining a movement path for slide frame 173 along longitudinal axis X-X. As shown in FIG. 14, the side walls may comprise interior surfaces that are slidably engageable with exterior surfaces of slide frame 173, allowing it to be slid back and forth within cavity 182. An end wall of interior cavity 182 may interlock with a corresponding surface of slide frame 173 to resist lateral forces applied thereto. To define the end wall, a central one of supports 185 may project outwardly from hand body 172 relative to other supports 185 and interior ones of supports 185 may be located upwardly from hand body 172 relative to the other supports 185. Channel 183 may extend through hand body 172 to along longitudinal axis X-X to guide member 125 into cavity 182 toward slide frame 173 through channel 179 of base 171.

Figure 15:
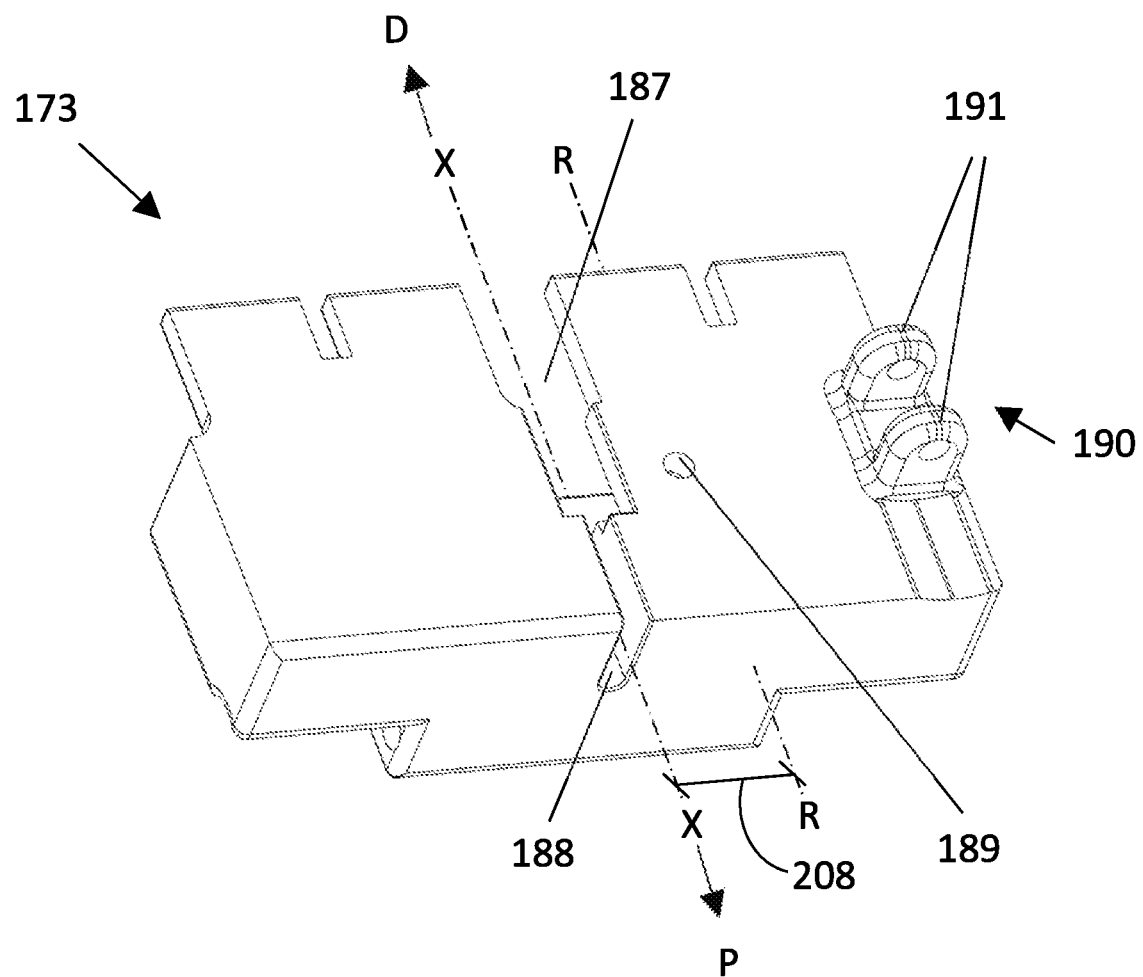
FIG. 15 depicts an exemplary slider for the FIG. 12 hand.

As shown in FIG. 15, slide frame 173 may comprise a structure defining an interior cavity 187, an output member receiving channel 188, a rocker attachment opening 189, and an upper thumb hinge 190. The structure of slide frame 173 may extend along a longitudinal axis X-X that may be coaxial with longitudinal axis X-X of hand body 172 when slide frame 173 is received within interior cavity 182. Interior cavity 187 may be sized to receive rocker 176 and accommodate a range of rotational motion for rocker 176 relative to frame 173. Output member receiving channel 188 may divide a palm-facing wall of slide frame 173 into different portions and provide structures engageable with the end of output member 125, including any structures similar to openings 116, 153 and channels 117, 154 described above. As shown in FIG. 15, output member receiving channel 188 may extend along longitudinal axis X-X so that output member 125 may be aligned with axis X-X when frame 173 is received in body 172. Rocker attachment opening 189 may be aligned with a rocker axis R-R that is generally parallel to and offset from longitudinal axis X-X by a distance 208. Upper thumb hinge 190 may comprise proximal supports 191 that are located on one side of slide frame 173 and define openings extending along an axis that is generally parallel with axis X-X.

Figure 16:
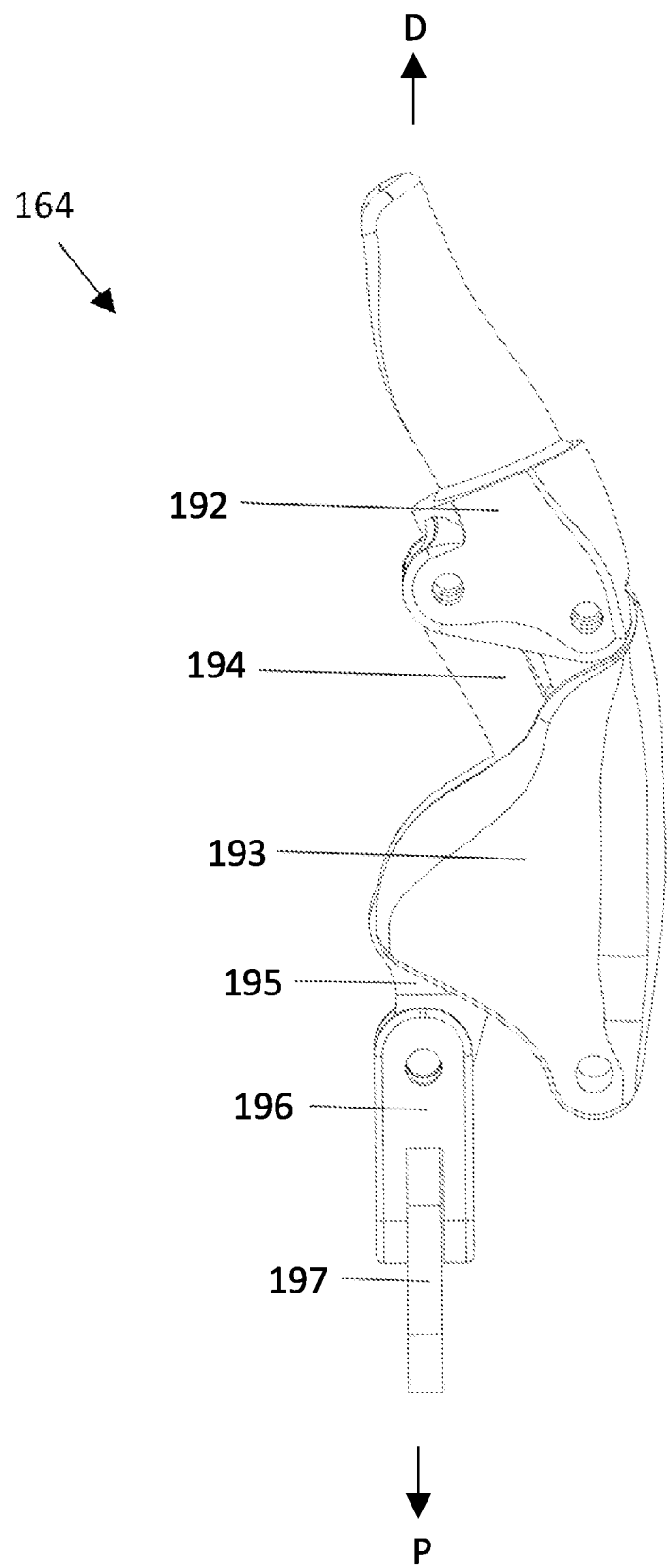
FIG. 16 depicts an exemplary finger digit for the FIG. 12 hand as being extended.

Finger digit assembly 174 may comprise finger digits 164 and various links that are pivotally engaged therewith and operable responsive to the output forces from output member 125. As shown in FIG. 16, for each finger digit 164, the links may comprise a first finger link 192, a second finger link 193, a third finger link 194, a fourth finger link 195, an adaptive grasp coupler 196, and a rocker connector 197. Each link of each digit 164 may comprise structures that are pivotally engageable with one another and/or hand body 172. For example, the respective structures of: (i) first finger link 192 may define finger-shaped exterior surfaces, a distal end comprising a tip portion with grip surfaces, and a proximal end engageable with second finger link 193 and third finger link 194; (ii) second finger link 193 may define finger-shaped exterior surfaces, a distal end engageable with the proximal end of first finger link 192, an interior portion engageable with fourth finger link 195, and a proximal end engageable with hand body 172; (iii) third finger link 194 may define a distal end engageable with the proximal end of first finger link 192 and a proximal end engageable with fourth finger link 195; (iv) fourth finger link 195 may define a distal end engageable with the interior portion of second finger link 193, an interior portion engageable with the proximal end of third finger link 194, and a proximal end engageable with adaptive grasp coupler 196; (v) adaptive grasp coupler 196 may define a distal end engageable with the proximal end of fourth finger link 195 and a proximal end engageable with rocker finger connector 197; and (vi) rocker finger connector 197 may define a proximal end engageable with adaptive grasp coupler 196 and a distal end engageable with rocker 176.

Figure 17:
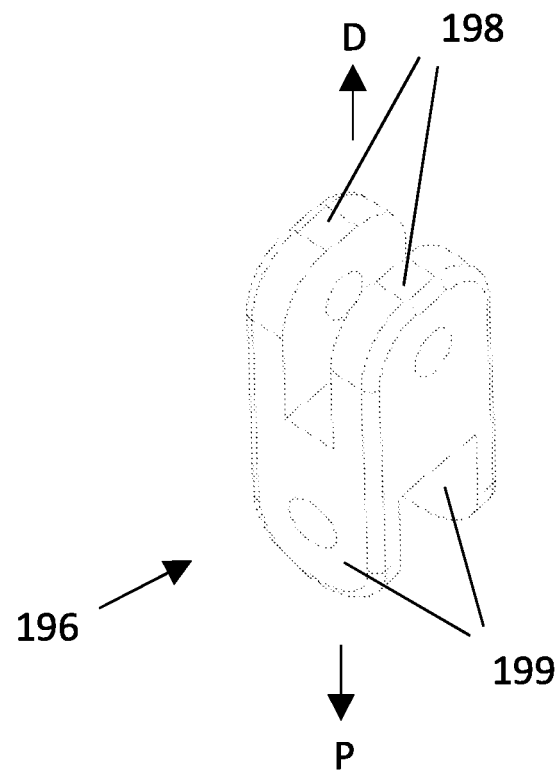
FIG. 17 depicts an exemplary coupler for the FIG. 12 hand.
Figure 18:
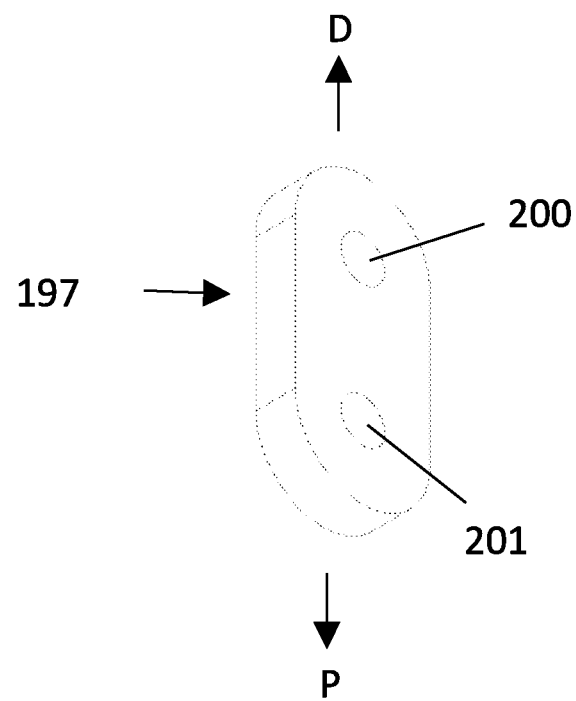
FIG. 18 depicts an exemplary connector for the FIG. 12 hand.

Each link may permit different types of movement. Some links may permit rotational movement about a lateral axis of hand body 172, such as when rotating toward or away from hand body 172. As shown in FIG. 17, the distal end of adaptive grasper coupler 196 may comprise distal supports 198 that are rotatably engageable with the proximal end of fourth finger link 195 so that coupler 196 and link 195 are rotatable about the lateral axis of hand body 172. Some links may permit rotational movement about a different axis. As also shown in FIG. 17, the proximal end of coupler 196 may comprise proximal supports 199 that are rotatably engageable with the distal end of connector 197 so that coupler 196 and connector 197 are rotatable about an axis that intersects the aforementioned lateral axis, allowing rocker 176 to move along the lateral axis. As shown in FIG. 18, each rocker connector 197 may comprise a distal opening 200 and a proximal opening 201.

Figure 19:
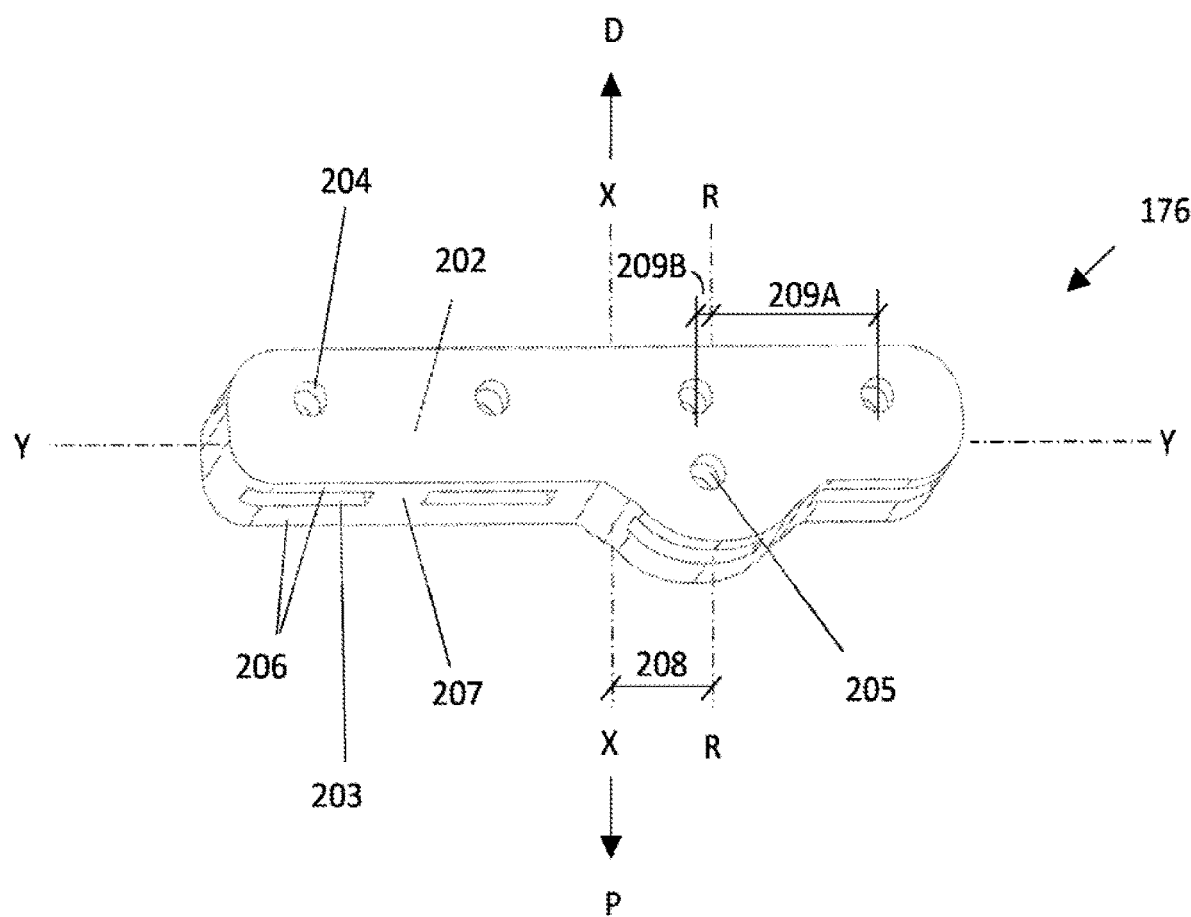
FIG. 19 depicts an exemplary rocker for the FIG. 12 hand.

Rocker 176 may be pivotally engageable slide frame 173 and the proximal end of each rocker finger connector 197 of each finger digit 164. As shown in FIG. 19, rocker 176 may comprise a structure defining an interior cavity 202, a plurality of passages 203 extending into cavity 202, and a plurality of coupler attachment openings 204, and a slide frame attachment opening 205. Interior cavity 202 may be defined by a pair of opposing sidewalls 206 joined by spacers 207. Each passage 203 may extend into cavity 202 between spacers 207, and each opening 204 and 205 may extend through sidewalls 206 and cavity 202. As shown in FIG. 19, longitudinal axes X-X of hand body 172 and slide frame 173 may extend through slide frame 173 when engaged with frame 173. Openings 204 may be aligned with a lateral axis Y-Y of rocker 176 that is non-parallel with axes X-X. In keeping with above, slide frame attachment opening 205 may be aligned with rocker axis R-R of rocker attachment opening 189. As shown in FIG. 19, rocker axis R-R may be offset from longitudinal axis X-X by distance 208 (e.g., as also shown in FIG. 15). One opening 204 may be associated with a pointer finger digit of finger digits 164 (e.g., digit 220 in FIG. 12) and offset from rocker axis R-R by a distance 209A. Another opening 204 may be associated with a middle finger digit of finger digits 164 (e.g., digit 221 in FIG. 12) and offset from axis R-R by distance 209B. Similar distances may be defined for other digits 164 and openings 204.

Figure 20:
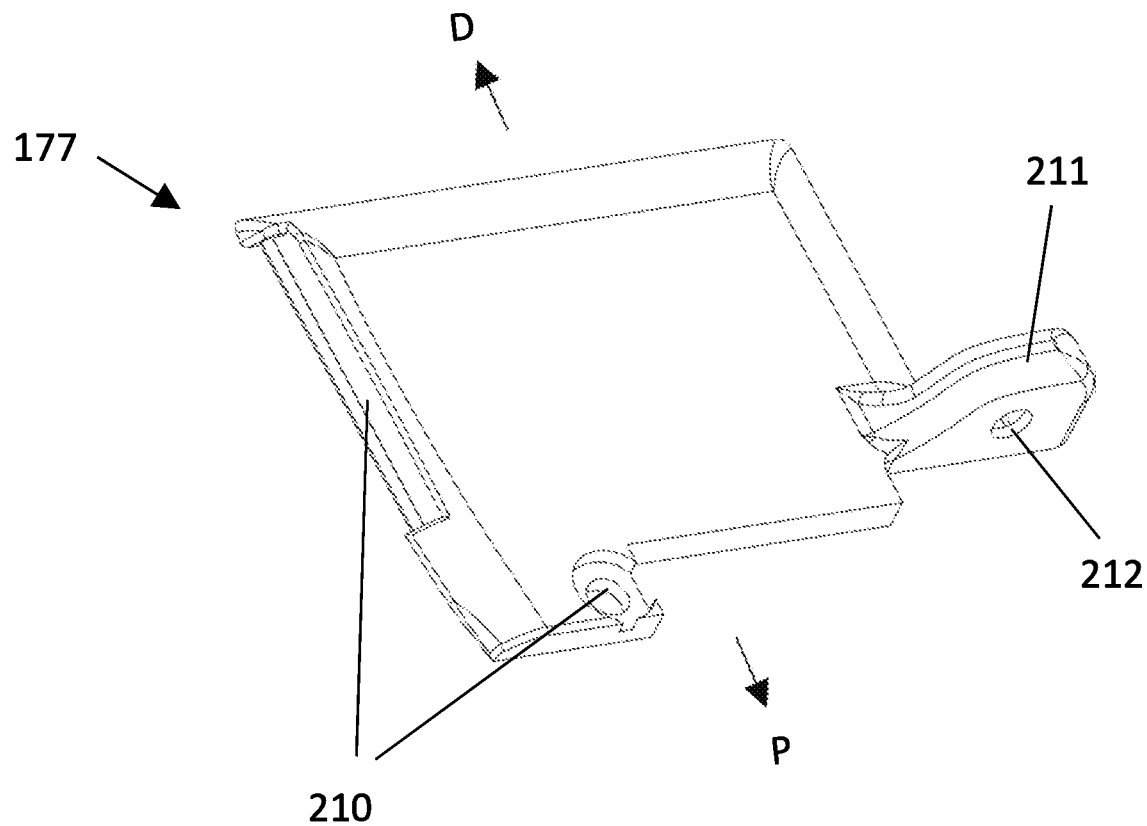
FIG. 20 depicts an exemplary cover for the FIG. 12 hand.

Cover 177 may be pivotally engaged with and/or secured to hand body 172. As shown in FIG. 20, cover 177 may comprise may comprise a structure defining cover securing elements 210 and a lower thumb hinge 211. Cover securing elements 210 may be engageable with cover securing elements 180 of hand body 172. For example, elements 210 may comprise an elongated hinge portion engageable with the elongated hinge portion of elements 180 to permit rotation of cover 177 relative to hand body 172, and one or more openings engageable with the one or more openings of elements 180 to secure cover 177 onto hand body 172. Lower thumb hinge 211 may comprise an opening 212 extending there through.

Thumb digit assembly 178 may be rotatably engageable with upper thumb hinge 190 of slide frame 173, thumb hinge base 184 of hand body 172, and lower thumb hinge 211 of cover 177. Thumb digit assembly 178 may comprise a thumb digit 213 and various links that are pivotally engaged therewith and operable responsive to the output forces from output member 125. As shown in FIG. 13, the links may comprise a first thumb link 214 and a second thumb link 215. For example, the respective structures of: (i) thumb digit 213 may define thumb-shaped exterior surfaces, a distal end comprising a tip portion with grip surfaces, and a proximal end engageable with first link 214 and second link 215; (ii) first thumb link 214 may define a proximal end engageable with digit 213 and link 215 and a distal end engageable with upper thumb hinge 190; and (iii) second thumb link 215 may define thumb-shaped exterior surfaces, a proximal end engageable with base 184 and hinge 211, and a distal end engageable with the digit 213 and link 214.

Each link may permit different types of rotational movement. As shown in FIG. 13, the distal end of second thumb link 216 may comprise first supports, the proximal end of thumb link 215 may comprise a second supports receivable between the first supports, and the proximal end of first thumb link 214 may be receivable between the first and second supports so that digit 213 is rotatable in first directions toward and away from hand body 172. Thumb hinge base 184 may be similarly engageable with the proximal end of second link 215 so that thumb digit 213 is rotatable in second directions relative to hand body 172.

The distal end of first thumb link 214 may be engageable with upper thumb hinge portion 190 and thus movable with slide frame 173 to operate thumb digit 213. For example, the distal end of link 214 may comprise first supports and a pin extending therebetween, upper thumb hinge portion 190 may comprise second supports, and link 214 may further comprise a connector 216 that is receivable between the first and second supports so that thumb digit 213 is rotatable outwardly from hand body 172 when slide frame 173 is proximate to base 171 and rotatable toward hand body 172 when slide frame 173 is distal of base 171. Accordingly, thumb digit 213 may be moved in the first directions when slide frame 173 is moved responsive to the output forces from output member 125 and/or manually moved in the second directions responsive to additional forces applied thereto by the user.

Methods of assembling terminal unit apparatus 160 are now described with reference to an assembly method 400. Method 400 may comprise any steps for configuring the force transfer elements of prosthetic hand 163, including one or more of: (i) fixedly engaging hand body 172 with hand base 171 (a step 410); (ii) rotatably engaging finger digit assembly 174 with hand body 172 and rocker 176 (a step 420); (iii) rotatably engaging rocker 176 with slide frame 173 (a step 430); (iv) fixedly engaging output member 125 with slide frame 173 (a step 440); (v) slidably engaging slide frame 173 with hand body 172 (a step 450); (vi) fixedly engaging cover 177 with hand body 172 (a step 460); (vii) rotatably engaging thumb assembly 178 with hand body 172 (a step 470); and/or (viii) causing a first portion of the plurality of digits to move toward the hand body faster than a second portion of the plurality of digits (a step 480).

As shown in FIG. 13, step 410 may comprise using an adhesive, screws, and/or another attachment element to fixedly engage a proximal surface of base 171 with a distal surface of hand body 172. Step 420 may comprise utilizing pins to rotationally engage the various links associated with finger digits 164, hand body 172, and/or rocker 176. In keeping with above, for example, step 420 may comprise inserting different pins through various openings to engage: the proximal ends of first finger links 192 with the distal ends of second finger links 193 and third finger links 194; the interior portions of second links 193 with distal ends of fourth finger links 195, and the proximal ends of second links 193 with finger digit portion 181; the proximal ends of third links 194 with the interior portions of fourth finger links 195; the proximal ends of links 195 with the distal ends of adaptive grasp couplers 196; and/or the proximal ends of couplers 196 with rocker 176.

Step 430 may comprise utilizing a pin to rotationally engage rocker 176 with slide frame 173. For example, step 430 may comprise rotating finger digit assembly 174 away from hand body 172, receiving rocker 176 within interior cavity 187 of slide frame 173, aligning rocker attachment opening 189 of slide frame 173 with slide frame attachment opening 205 of rocker 176, and receiving the pin in openings 189 and 205. Step 440 may comprise receiving output member 125 in channel 188 of slide frame 173, routing output member 125 through channel 183 of hand body 172, and/or routing output member 125 through channel 179 of base 171. For example, step 440 may comprise engaging an end of output member 125 with a catchment opening in communication with channel 188.

Figure 23:
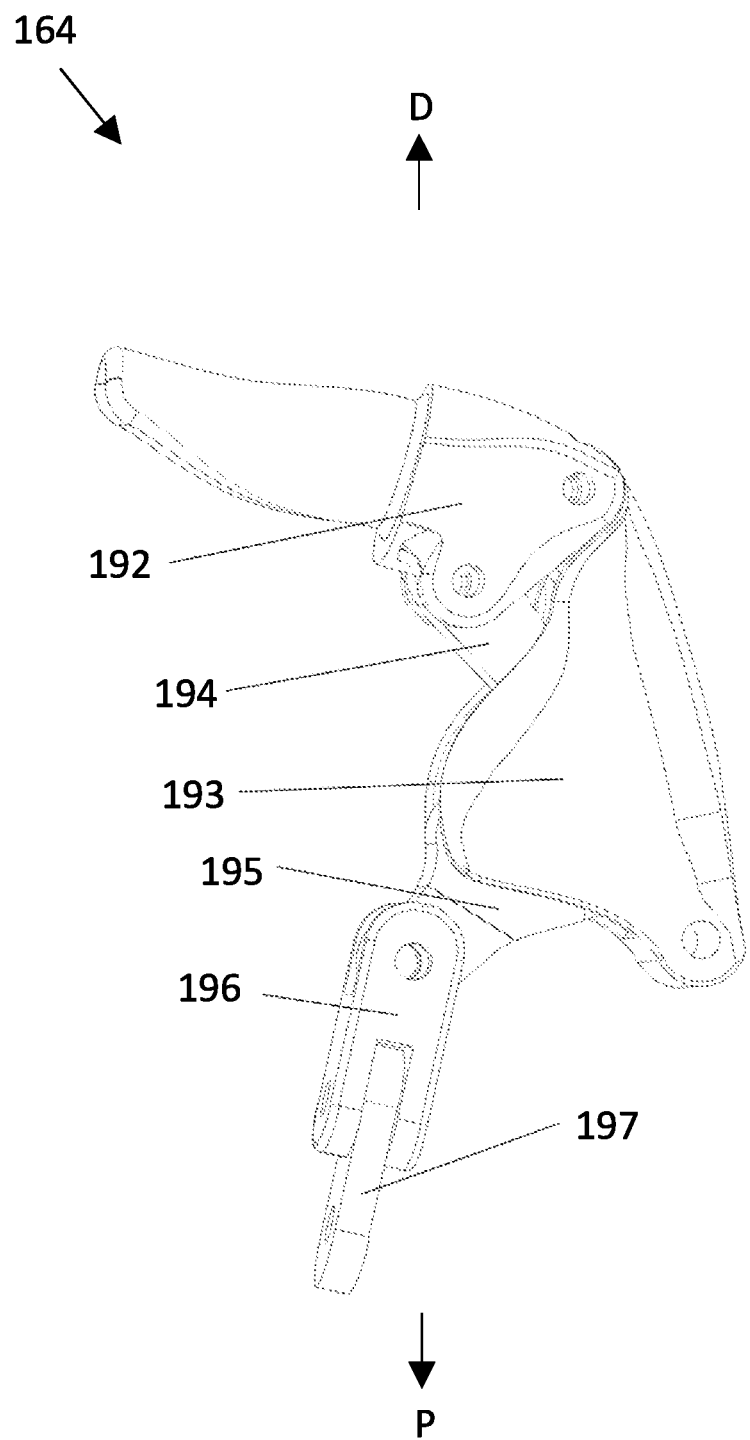
FIG. 23 depicts the FIG. 16 finger as being retracted.

Step 450 may comprise rotating finger digit assembly 174, rocker 176, slide frame 173, and output member 125 engaged therewith toward hand body 172 about the elongated pin until slide frame 173 is received in interior cavity 182 of hand body 172. At this point in method 400, exterior surfaces of slide frame 173 may be slid in proximal and distal directions within interior cavity 182 between a distal position where finger digits 164 are fully extended (e.g., as shown in FIG. 16) and a proximal position where digits 164 are fully contracted (e.g., as shown in FIG. 23). Step 460 may comprise engaging the elongated hinge portion of hand body 172 with the elongated hinge portion of cover 177, aligning the openings of lower thumb hinge 211 of cover 177 and thumb hinge base 184 of hand body 172, and receiving screws or like means the one or more openings of hand body 172 and cover 177. In this regard, cover 177 may be utilized to seal cavity 182, confine the path of movement for slide frame 173, and/or maintain output member 125 within channel 188 of slide frame 173.

Step 470 may comprise utilizing pins to rotatably engage the proximal end of thumb digit 213 with the distal ends of first thumb link 214 and second thumb link 215, the distal end of first link 214 with an end of connector 216, and the other end of connector 216 with distal supports 191 so that so that thumb digit 213 is rotatable in proximal-distal directions toward and away from hand body 172 responsive to movements of slide frame 173. Step 470 may further comprise aligning the openings extending through thumb hinge base 184 and the proximal end of second link 215 so that digit 213 is rotatable in medial-lateral directions relative to hand body 172. At this point in method 400, the testing force may be applied to output member 125 during step 480 for the purpose of opening and closing terminal unit apparatus 160 with member 125. For example, step 480 may comprise maintaining a position of terminal unit apparatus 160 (e.g., by securing it to a bench) and pulling on output member 125 until finger digits 164 and thumb digit 213 are moved toward hand body 172.

Once terminal unit apparatus 160 has been assembled according to method 400, then it may be utilized to grip objects with finger digits 164. The force transfer elements of prosthetic hand 163 described above may be configured for different types of grips. For example, in keeping with above, the force transfer elements of prosthetic hand 163 may be configured to perform an "adaptive grip" in which a first portion of finger digits 164 are moved toward hand body 172 at a first rate, a second portion of digits 164 are moved toward hand body 172 at a second rate, and the first rate is faster than the second rate so that apparatus 160 closes in more hand-like manner.

Figure 21:
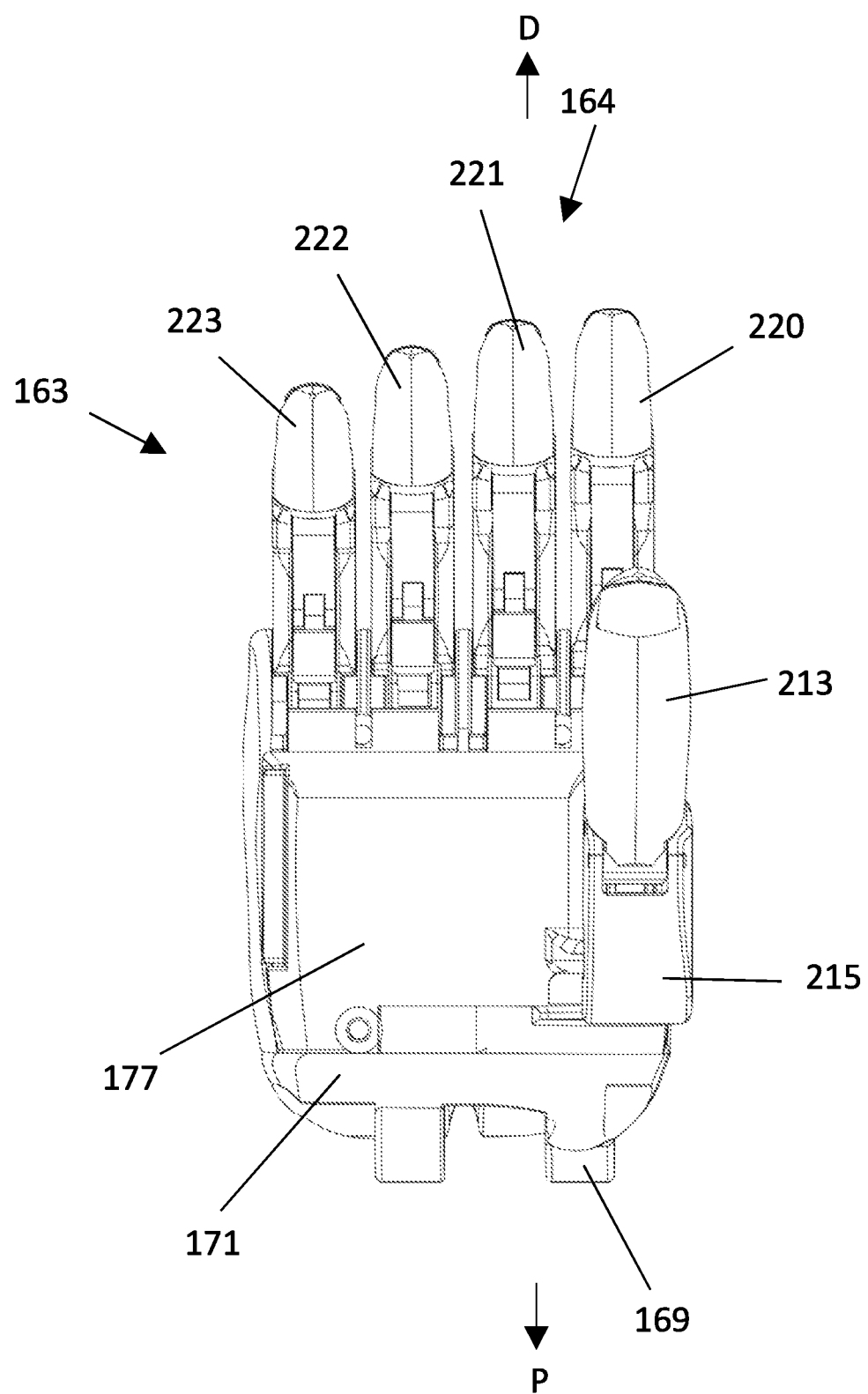
FIG. 21 depicts a palm-facing view of the FIG. 12 hand in an open position.

As shown in FIG. 12, finger digits 164 may comprise: a pointer finger digit 220; a middle finger digit 221; a ring finger digit 222; and a pinky finger digit 223. Prosthetic hand 163 may be operable between an open position, a closed position, and a plurality of intermediate positions. An exemplary open position of hand 163 is shown in FIG. 21, in which finger digits 220-223 and thumb digit 213 are fully extended. The open position may be the default position. For example, output member 125 and/or any of the various links and/or structures described above may be configured bias each of digits 220-223 and 213 toward its fully extended position. As a further example, various resilient elements (e.g., elastic bands or springs) may be used to apply biasing forces to the links and/or structures.

An exemplary closed position of hand 163 is shown in FIG. 12, in which finger digits 220-223 and thumb digit 213 are closed. The closed position may be realized when a maximum output force is applied by output member 125. The maximum output force may be applied to slide frame 173, causing frame 173 and rocker 176 engaged therewith to slide proximally within interior cavity 182. When sliding proximally, rocker 176 may apply proximally directed forces to couplers 196 and connectors 197, which transfer the forces to the distal ends of fourth finger links 195, causing them to rotate about the interior portions of second finger links 193. As shown in FIG. 23, the rotations of fourth links 195 may transfer the proximally directed forces to third finger links 194, which may then act through first links 192, second links 193, and hand body 172 to close finger digits 164.

Figure 22:
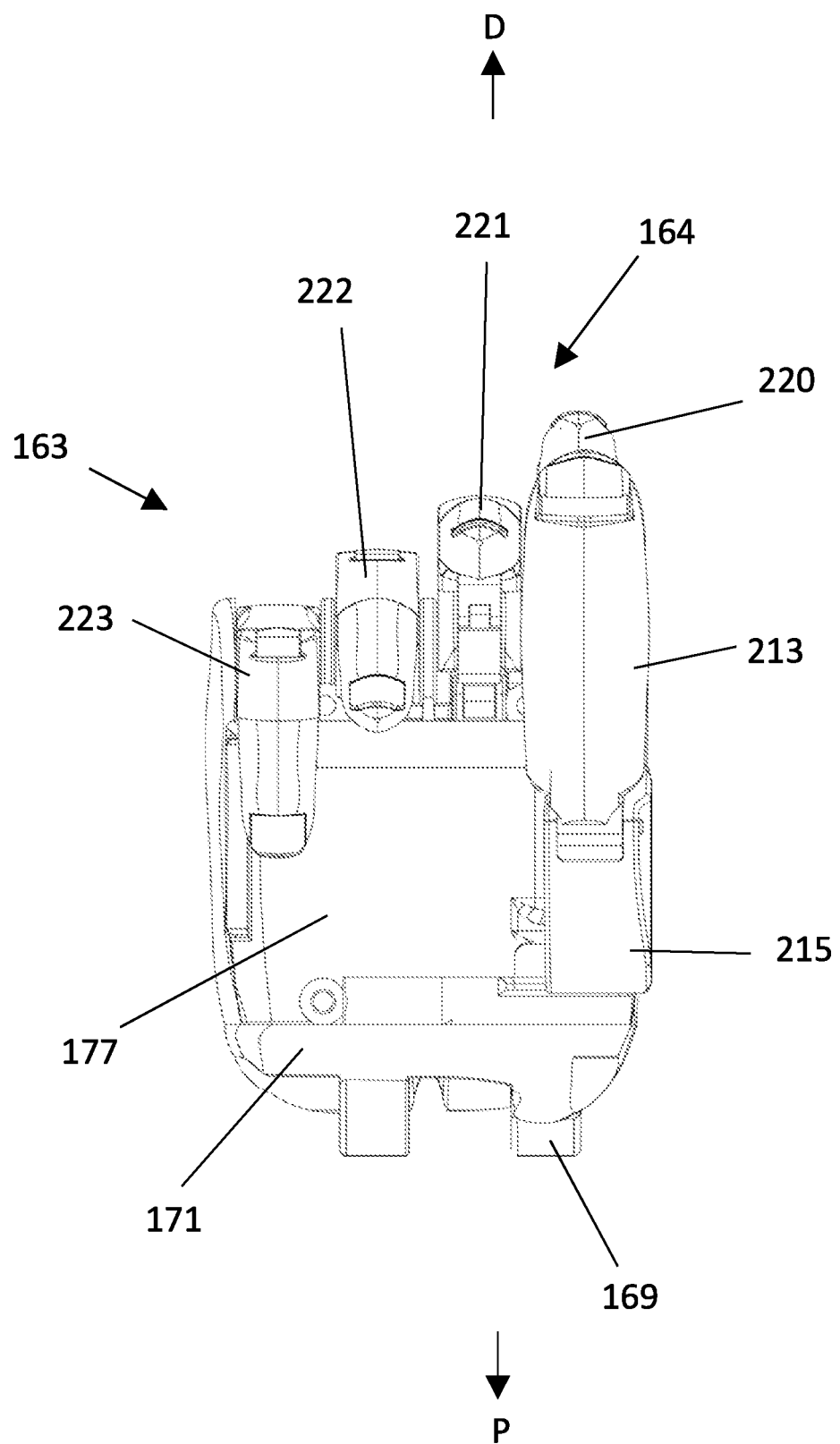
FIG. 22 depicts the FIG. 21 hand in a closed position.
Figure 24:
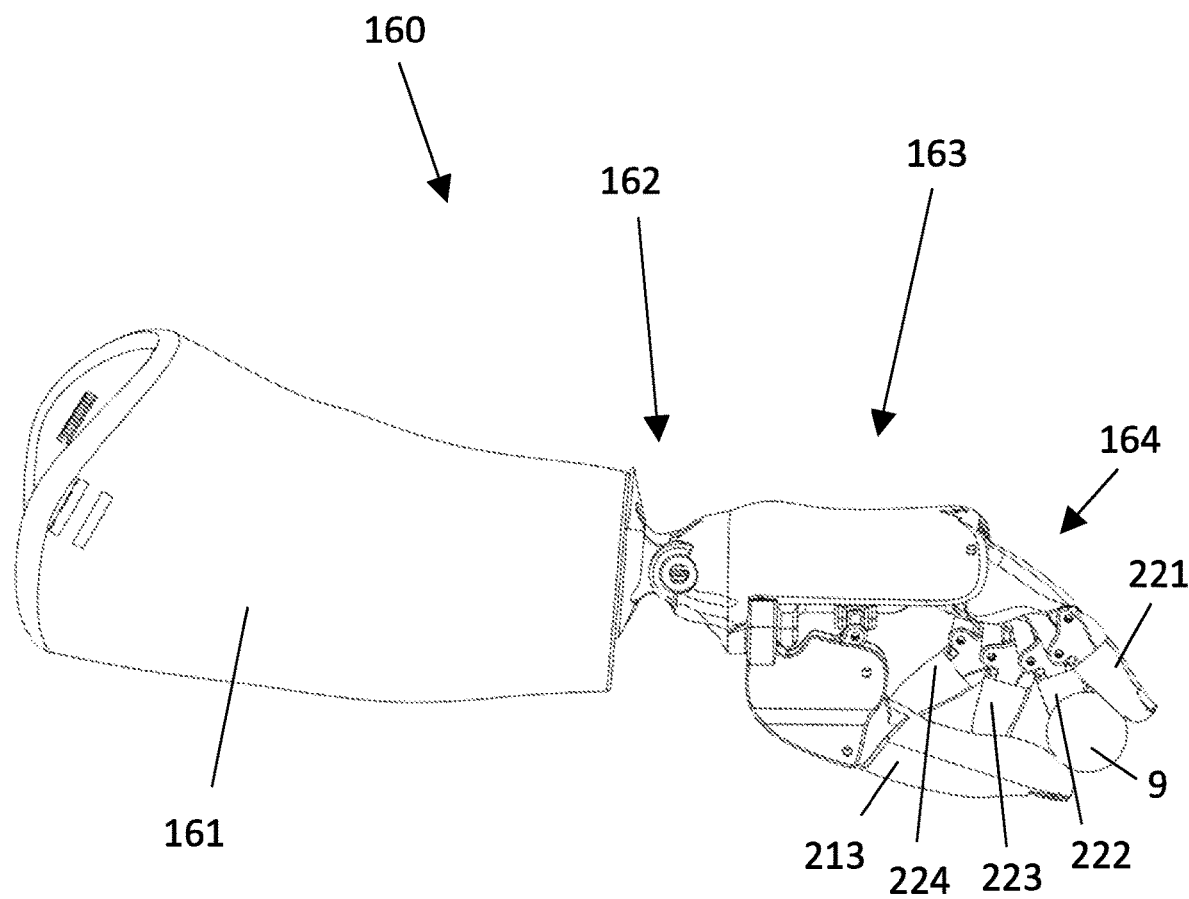
FIG. 24 depicts a side view of the FIG. 12 hand grasping an exemplary object.

As shown in FIGS. 22 and 24, each finger digit 220-223 may close at different rates of speed and with different degrees of closure. First or pointer finger digit 22 may rotate faster and close to a greater degree than digits 221, 222, and/or 223 so that the grasp surfaces of finger digit 220 may contact the grasp surfaces of thumb digit 213 when hand 163 is in the closed position. Second or middle finger digit 221 may rotate slower and close to a lesser degree than first digit 220, and/or third or ring finger digit 222 may rotate slower and close to a lesser degree than second digit 221, allowing hand 163 to assume a more life-like position in the closed position. Because of its smaller size, fourth or pinky finger digit 223 may rotate faster and close to a greater degree than each of digits 221, 222 and/or 222.

As shown in FIG. 19, the different rates of speed and degrees of closure may be determined by the spacing between coupler attachment openings 204 and slide frame attachment opening 205 along lateral axis Y-Y of rocker 176. For example, the output forces may be applied from output member 125 to slide frame 173 along longitudinal axis X-X, and then transferred from slide frame 173 to rocker 176 along rocker axis R-R. Each opening 204 and thus each rocker connector 197 may be spaced apart from rocker axis R-R along axis lateral Y-Y by different distances so that the output forces are applied differently by rocker 176 to each finger digit 220-223. Opening 204 for connector 197 of point finger digit 220 may be spaced apart from rocker axis R-R by distance 209A, opening 204 for connector 197 of middle finger digit 221 may be spaced apart from axis R-R by distance 209B, and distance 209A may be greater than distance 209B so that the output forces transferred to first or pointer finger digit 220 are different from the output forces transferred to second or middle finger digit 221, causing digits 220 and 221 to close at different rates of speed and/or to a different degree. The same can be said of each finger digit 222 and 223, both of which may be spaced further apart from axis R-R along axis Y-Y, causing them to close at different rates and degrees.

The rotatable engagement between slide frame 173 and rocker 176 also may allow hand 163 to further adapt when grasping an object. As shown in FIG. 24, the grasping surfaces of pointer finger digit 220 and thumb digit 213 may be utilized to grasp an exemplary object 9 (e.g., a ping pong ball). Hand 163 may be moved toward object 9 in the open position (e.g., as shown in FIG. 22) until object 9 is located proximate to pointer finger digit 220 and thumb digit 213, which may be rotated laterally as needed to locate the grasp surfaces of digit 220 opposite of the grasp surfaces of digit 213. The output forces from output member 125 may then be applied to rocker 176 by slide frame 173, causing digits 220 and 213 to move toward one another until their grasp surfaces make contact with object 9. At this point, reaction forces applied by object 9 may be greater than closing forces applied by digits 220 and 213, causing the output forces and a portion the reaction forces to be redistributed back to digits 221-223 with rocker 176 until a state of equilibrium is reached. As shown in FIG. 24, the reaction forces from object 9 may cause digits 221-223 close fully before a maximum amount of force may be applied to object 9; after which, the maximum amount of force may be applied.

Exemplary methods of assembling system 100 are now described with reference to an assembly method 500. For example, method 500 may comprise one or more of: (i) assembling apparatus 130 and apparatus 160 (a step 510); (ii) engaging input member 120 with harness 102 and apparatus 130 (a step 520); (iii) engaging output member 125 with apparatus 130 and 160 (a step 530); (iv) wearing harness 102 on body 2 (a step 540); (v) wearing apparatus 130 on proximal portion 5 of partial arm 4 (a step 550); (vi) wearing apparatus 160 on distal portion 7 of partial arm 4 (a step 560); (vii) generating output forces by performing operative movements of partial arm 4 relative to body 2 (a step 570); and/or (viii) causing prosthetic hand 163 to move between the open and closed positions responsive to the operative movements (a step 580).

Steps 510 and 520 may be performed according to methods 300 and 400. Step 530 may be performed according to the structures of harness 102 described above. According to FIGS. 1 and 2, step 520 may comprise inserting arm 3 into an opening defined by strap 104 and placing length 112 of strap 106 over the shoulder of arm 4. Step 550 may comprise engaging length 114 with clip 113 and support 131, and tightening length 114 until the position of support 131 is generally fixed relative to proximal portion 5 of arm 4. Step 560 may comprise receiving distal portion 7 of arm 4 within socket 161, engaging strap 167 with support 131 and socket 161, and tightening strap 167 until the position of socket 161 and thus apparatus 160 is generally fixed relative to distal portion 7. Step 570 may comprise performing any type of operative movements. For example, step 570 may comprise moving terminal unit apparatus 160 distally until the input forces are applied to force amplification apparatus 130 as described above. Step 580 may likewise be performed according to the various structures described above.

The combination of force amplification apparatus 130 and terminal unit apparatus 160 may be required in system 100, especially when used by smaller humans who could not otherwise generate an input force large enough to operate apparatus 160. For example, to make them smaller- or child-sized, the structures of prosthetic hand 163 describe above (e.g., slide frame 173, rocker 176, etc.) may need to be very compact and tightly constructed. Additional friction forces may be generated as a result, meaning that even prosthetic hand 163 may require a minimum operating force that is beyond the normal capabilities of some children. Force amplification apparatus 130 solves this problem by making better use of the available input forces. Similar benefits may be realized with any terminal unit apparatus 160.

Figure 25:
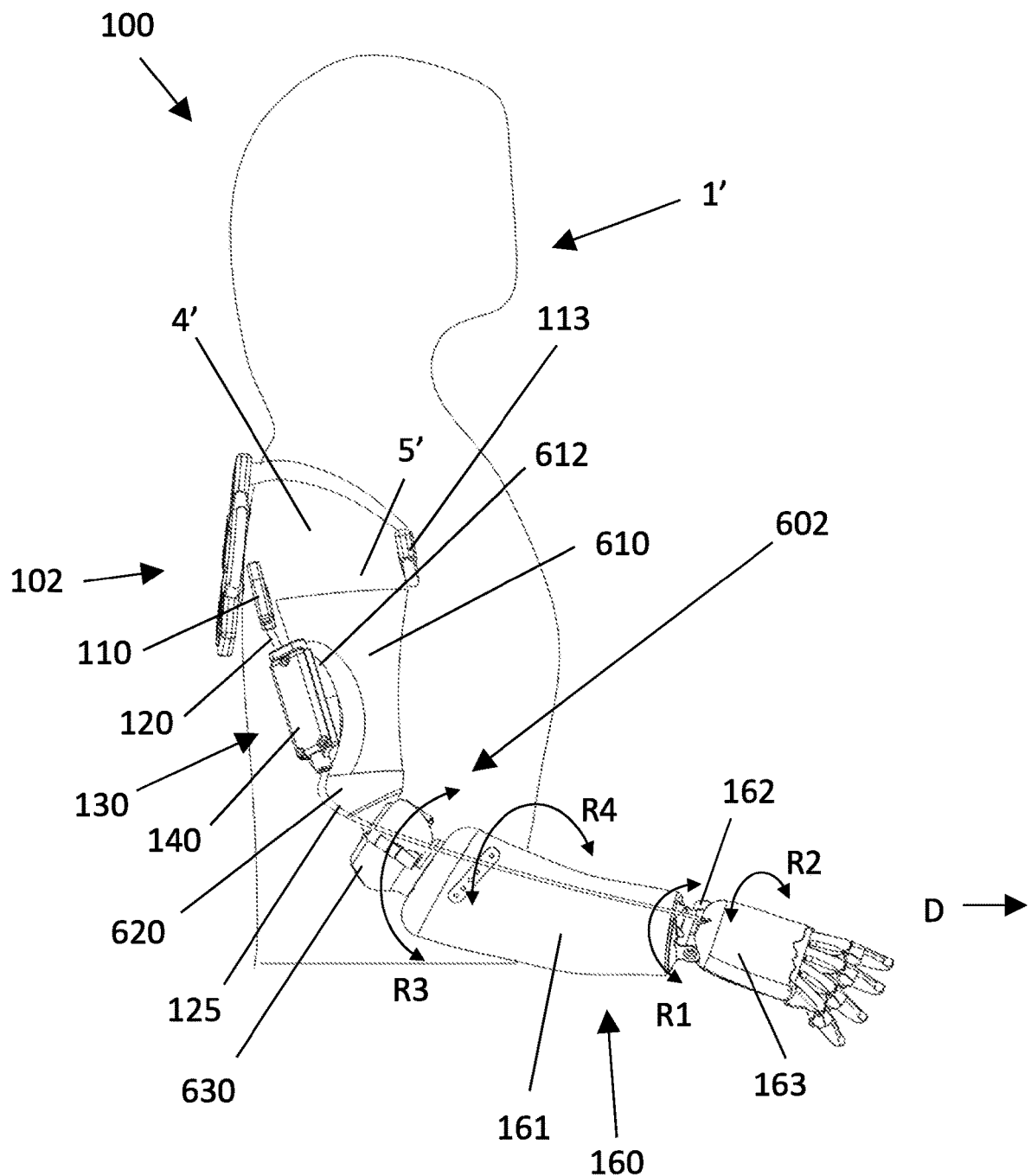
FIG. 25 depicts a side view of another exemplary upper arm prosthetic system comprising a force amplification apparatus, an adjustable elbow apparatus, and a terminal unit apparatus.

Additional aspects of this disclosure are now described with reference to an exemplary upper arm prosthetic system 600 for human subject 1. Upper arm system 600 may comprise elements from upper arm system 100 described above plus an adjustable elbow apparatus 602 for use with a human subject 1' having an partial arm 4' with a proximal portion 5' that comprises a partial humerus bone but does comprise elbow 6 (e.g., as in FIG. 1). As shown in FIG. 25, elbow apparatus 602 may comprise a proximal arm prosthetic 610, a proximal elbow portion 620, and a distal elbow portion 630.

Figure 26:
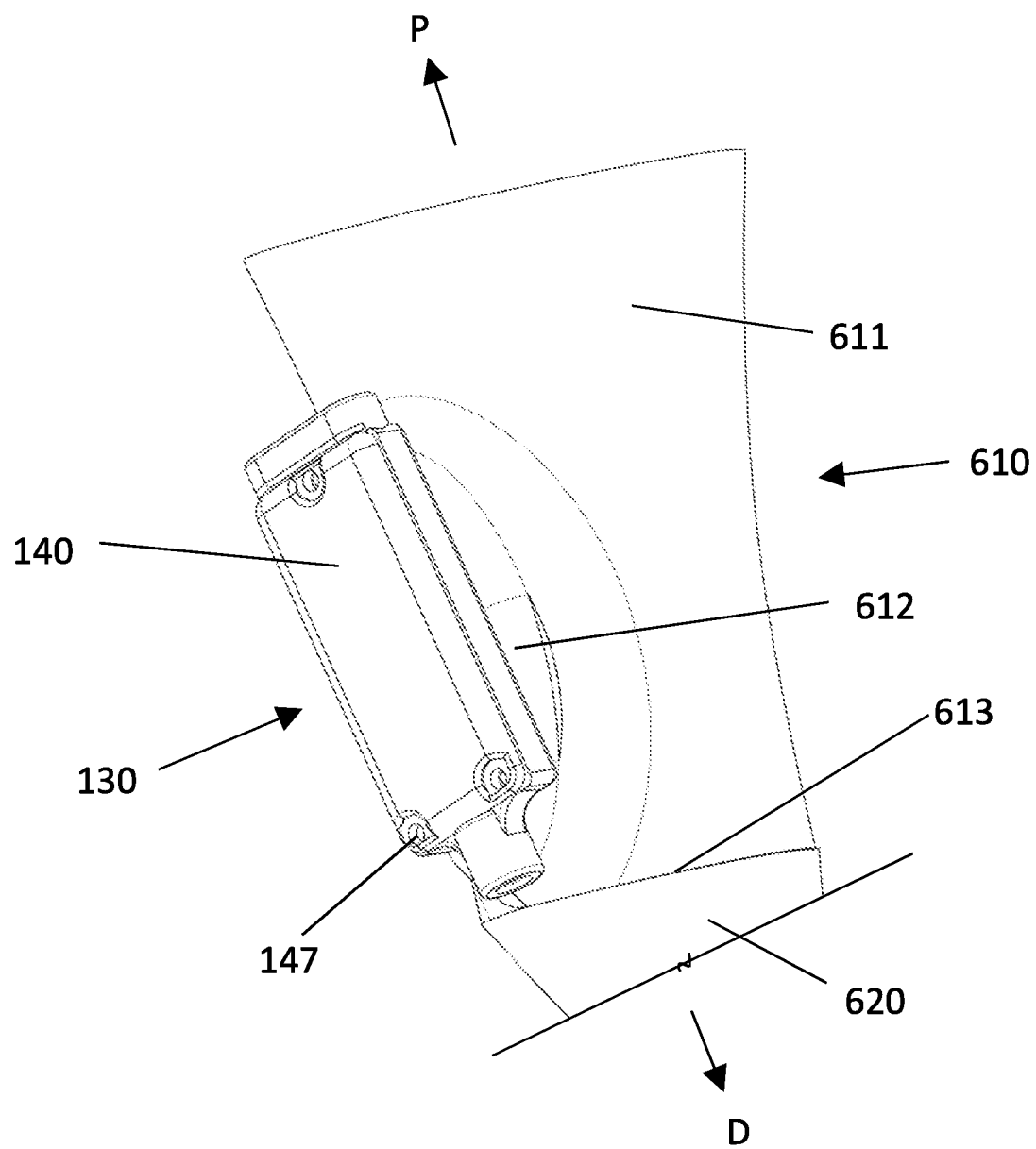
FIG. 26 depicts a proximal arm prosthetic of the FIG. 25 elbow apparatus.

As shown in FIG. 26, proximal arm prosthetic 610 may comprise structures defining a socket 611, a raised platform 612, and distal interface 613. Socket 611 may comprise an interior cavity configured to receive proximal portion 5'. For example, exterior surfaces of proximal portion 5' may be approximated or scanned to create an anatomical data set, and the interior cavity may be formed or printed based on the anatomical data set to obtain a more precise fit with proximal portion 5'. As shown in FIG. 25, a distal end of socket 611 may be engageable with clip 110 and/or bi-directional clip 113 using one or more straps (e.g., like strap 106) to maintain a position of socket 611 relative to proximal portion 5' similar to as described above. Any form of engagement with harness 102 may be used.

Raised platform 612 may be similar to raised platform 137 described above. As shown in FIG. 25, force amplifier 140 of amplification apparatus 130 may be rotatable engaged with raised platform 612 using opening 147 in a similar manner; and platform 612 may be similarly offset from an environment-facing surface of socket 611 by a distance that permits force amplifier 140 to rotate freely. Distal interface 613 may be engageable with proximal elbow portion 620 by any means, including adhesives, interlocking structures, screws, and the like.

Figure 27:
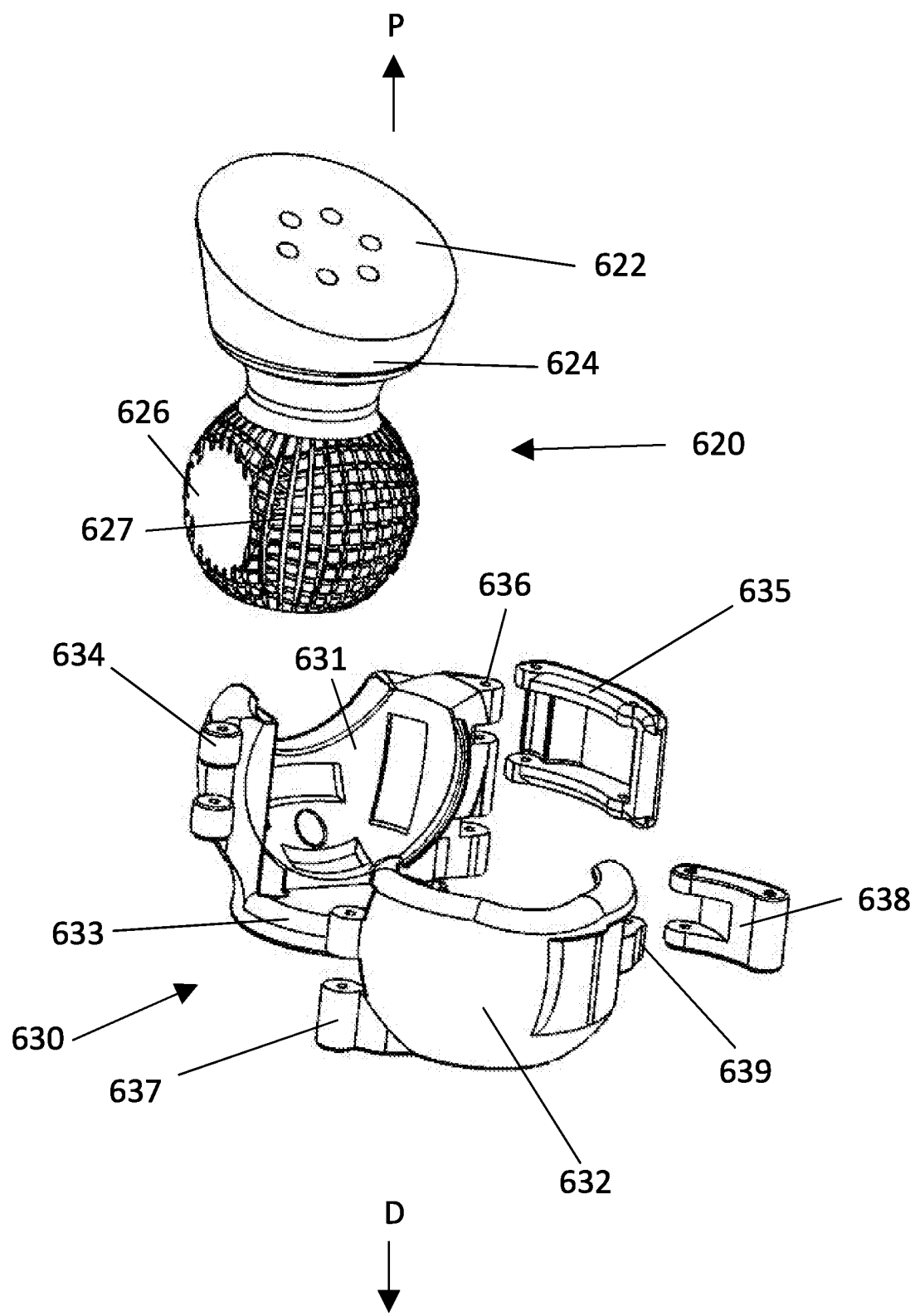
FIG. 27 depicts an exploded view of the FIG. 25 elbow apparatus.

As shown in FIG. 27, proximal elbow portion 620 may comprise a structure defining a proximal interface 622, an extension 624, and a distal interface 626. Proximal interface 622 may be engageable with distal interface 613 by any means. As shown in FIG. 27, interface 622 may comprise a plurality of openings. Extension 624 may extend proximally so that interface 613 is spaced apart from distal interface 626. As also shown in FIG. 27, distal interface 626 may comprise a spherical connector element comprising of an exterior connecting surface 627 configured to obtain a friction fit with distal elbow portion 630. Exterior surface 627 may comprise any form of intentional roughening and/or friction-promoting surface treatments. For example, exterior surface 627 may comprise a spherical grid of beam elements defining a set of raised portions and depressions. As a further example, surface 627 may defined entirely by the spherical grid of beam elements so that interface 626 has hollow interior to reduce the weight of elbow apparatus 602.

As further shown in FIG. 27, distal elbow portion 630 may comprise a first connection shell 631 and a second connection shell 632. First connection shell 631 may comprise a distal interface 633, a first shell hinge portion 634, and a first latch portion 635. Distal interface 633 may be engageable with a proximal end of socket 161 by any means. First connection shell 631 may comprise a structure defining part of an interior cavity sized to receive the spherical connector element of distal interface 626. As shown in FIG. 27, first shell hinge portion 634 may be located on one edge of shell 631 and first latch portion 635 may be rotatably engageable with first latch hinge structures 636 on an opposite edge of first shell 631. Second connection shell 632 may comprise a second shell hinge portion 637, and a second latch portion 638. Second shell 632 may comprise a structure defining another part of the interior cavity sized to receive the spherical connector element of distal interface 626. As shown in FIG. 27, second shell hinge portion 637 may be located on one edge of shell 632 and second latch portion 638 may be rotatably engageable with second latch hinge structures 639 on another edge of shell 632.

Exemplary methods of assembling adjustable elbow apparatus 602 are now described with reference to an exemplary assembly method 700. For example, method 700 may comprise one or more of: (i) fixedly engaging distal interface 613 with proximal interface 622 (a step 710); (ii) fixedly engaging distal interface 633 with terminal unit 160 (a step 720); (iii) rotatably engaging first hinge portion 634 with second hinge portion 637 (a step 730); (iv) rotatably engaging first latch portion 635 with latch structures 636 and second latch portion 638 with second latch structures 639 (a step 740); (v) engaging distal interface 626 with first shell 631 and second shell 632 (a step 750); and (iv) engaging first latch portion 635 with second latch portion 638 in order to maintain a position of distal elbow portion 630 relative to proximal elbow portion 620 (a step 760).

Steps 710 may comprise interlocking distal interface 613 with distal interface 62 by any means (e.g., with attachment elements). Step 720 may comprise interlocking a rim structure of distal interface 633 (e.g., a thread) with a corresponding structure within opening 165 of socket 161 (e.g., another thread). Steps 730 and 740 may comprise receiving pins in openings extending through hinge portions 634 and 637, latch portion 635 and structures 636, and latch portion 638 and structures 639. Step 750 may comprise locating the spherical connector element of distal interface 626 in the partial interior cavity of first shell 631 so that movements of elbow portion 630 relative to elbow portion 620 are at least partially restricted by an initial friction fit between exterior surfaces 627 and interior surfaces of shell 631. Step 750 also may comprise moving second shell 632 relative to first shell 631 until latch structures 636 are adjacent latch structures 639.

Step 760 may comprise engaging latch portion 635 with latch portion 638 so as to obtain a final friction fit between exterior surface 627 and the interior surfaces of shells 631 and 632 that maintains the position of elbow portion 620 relative to elbow portion 630. The spherical connector element of distal interface 626 may be compressed between shells 631 and 632 after completion of step 760 so as to enhance the friction fit obtained by exterior surface 627.

Method 700 may comprise additional steps for utilizing adjustable elbow apparatus 602 with upper arm prosthetic system 600, including any steps described above with reference to assembly methods 300, 400, and 500. Within system 600, steps 750 and 760 may be repeated to selectively position distal elbow portion 630 and terminal unit apparatus 160 relative to proximal elbow portion 620. The interior surfaces of first shell 631 may be configured to obtain a friction fit with exterior surfaces 627 that is sufficient to at least temporarily support the weight of portion 630 and terminal unit apparatus 160 before performing step 760, allowing the user to manually adjust those elements further during step 750 before locking them into position. In keeping with above, adjustable elbow apparatus 602 may thus be operable to selectively position terminal unit apparatus 160 between a plurality of different positions in a rotational direction R3 (e.g., toward and away from partial arm 4') and/or a rotational direction R4 (e.g., about a longitudinal axis of apparatus 160), much like a human elbow.

The addition of adjustable elbow apparatus 602 to the above-described elements from upper arm system 100 may allow system 600 to be utilized with yet another set of patients that would otherwise have diminished functionality. Because it does not restrict input member 120 or output member 125 in any way, the addition of elbow apparatus 602 may not adversely affect the performance of the elements of system 100, allowing elements such as force amplification apparatus 130 and terminal unit apparatus 160 to perform as described in system 100 or system 600. Moreover, because partial arm 4' of FIG. 25 lacks elbow 6, it may also lack a number of muscles associated therewith, making the role of force amplification apparatus 130 potentially more important in system 600 in some instances.

Without limiting the combined benefit of utilizing force amplification apparatus 130 together with terminal unit apparatus 160 within system 100 or 600, it is contemplated that apparatus 130, 160, and 602 also may be used independently without departing from this disclosure. For example, force amplification apparatus 130 may be utilized similarly within comparable prosthetic systems and/or with other types of terminal apparatus 160; and both of apparatus 160 and 602 may be used independently without any type of apparatus 130. Accordingly, aspects of each apparatus 130, 160, and/or 602 may be claimed individually as standalone inventions or together as part of one invention comprising system 100 or 600.

Assembly methods 300, 400, 500, and/or 700 also may comprise additional steps for making the various structures described above. For example, each structure of harness 102, force amplification apparatus 130, terminal unit apparatus 160, and adjustable elbow apparatus 602 may be composed of any biocompatible material, including any metallic materials, polymeric materials, and their equivalents. Any 3D printable biocompatible materials also may be used to help reduce the cost of any or all of these structures, making it easier to smaller persons in developing markets to access the benefits described herein. For example, each method 300, 400, 500, and 700 also may comprise a set of initial steps for: (i) receiving a kit comprising a set of non-printable parts and instructions for printing a set of locally made parts comprising any of the structures of described above for harness 102, apparatus 130, apparatus 160, and/or apparatus 602; (ii) printing the set of locally made parts from a 3D printable biocompatible material; and (iii) assembling any of harness 102, apparatus 130, apparatus 160, and/or apparatus 602 according to this disclosure.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

Embodiments in which an exclusive property or privilege is claimed are defined as follows:

1. A terminal unit apparatus for an upper arm of a human subject having a body and a partial arm extending from the body, the apparatus comprising:
a hand body wearable on the partial arm;
force transfer elements comprising
a slide frame that is slidably engageable with the hand body, engageable with an
output member, and slidable against surfaces of the hand body, and
a single rocker rotatably engageable with the slide frame;
finger digits rotatably engageable with the hand body and the single rocker; and
a thumb digit rotatably engageable with the slide frame and the hand body,
the force transfer elements being operable with output forces applied to the slide frame by
the output member to move the finger digits and the thumb digit toward and away from
the hand body by sliding the slide frame and the rocker relative to the hand body.

2. The apparatus of claim 1, wherein the output member is removably engageable with the slide frame.

3. The apparatus of claim 2, wherein the slide frame extends along a longitudinal axis of the hand body and the output member is aligned with the longitudinal axis.

4. The apparatus of claim 3, wherein the single rocker is rotatably engageable with the slide frame at a point that is laterally offset from the longitudinal axis.

5. The apparatus of claim 4, wherein the slide frame comprises an interior cavity sized to accommodate a range of rotational motion for the single rocker and the single rocker is rotatably engageable with the slide frame in the interior cavity.

6. The apparatus of claim 1, wherein the slide frame is slidable between:
a distal position relative to the partial arm, in which the finger digits and the thumb digit are moved away from the hand body; and
a proximal position relative to the partial arm, in which the finger digits and the thumb digit are moved toward the hand body.

7. The apparatus of claim 6, wherein the single rocker is rotatably engageable with the slide frame so that, when the movement of the fingers relative to the hand body is unrestrained by an object, a first portion of the finger digits move inwardly faster than a second portion of the finger digits when the slide frame is slid from the distal position to the proximal position.

8. The apparatus of claim 7, wherein one link of each finger digit of the finger digits is rotatably engageable with the single rocker at one position of a plurality of different positions that are spaced apart laterally from one another on the single rocker.

9. The apparatus of claim 8, wherein:
the plurality of different positions comprise
a pointer finger position associated with a pointer finger digit of the finger digits,
a middle finger position associated with a middle finger digit of the finger digits,
a ring finger position associated with a ringer finger digit of the finger digits, and
a pinky finger position associated with a pinky digit of the finger digits; and
the slide frame is rotatably connected to the single rocker at a rocker connection position located between the middle finger position and the pointer finger position.

10. The apparatus of claim 9, wherein the first portion of the finger digits comprises the pointer finger digit and the second portion of the finger digits comprises the pinky finger digit.

11. The apparatus of claim 10, wherein a first distance between the middle finger position and the rocker connection position is less than a second distance between the rocker connection position and the pointer finger position.

12. The apparatus of claim 1, wherein the output member comprises one of a beam, a cable, a rod, a shaft, or a wire.

13. The apparatus of claim 1, comprising a socket wearable on a distal portion of the partial arm, in which the hand body is rotatably engageable with the socket.

14. The apparatus of claim 13, comprising
a support wearable on the partial arm; and
a force amplifier that is rotatably engageable with the support and operable to apply the output forces to the output member when the partial arm is moved relative to the body.

15. The apparatus of claim 14, wherein, the force amplifier is operable to receive input forces from an input member engageable with a harness wearable on the body, amplify the input forces into the output forces, and transfer the output forces to the output member when the partial arm is moved relative to the body.

16. The apparatus of claim 15, wherein the force amplifier comprises:
a slider base that is rotatably engageable with the support and fixedly engageable with the input member;
a slider that is slidably engageable with the slider base and fixedly engageable with the output member; and
a pulley that is rotatably engageable with the slider,
wherein, when the harness, the support, and the socket are worn, and the partial arm is moved relative to the body:
the pulley is operable to transfer the input forces from the input member to the slider; and
the slider base is rotatable relative to the support to maintain a generally linear alignment between the input member and the force amplifier.

17. The apparatus of claim 16, wherein the partial arm comprises a partial humerus bone without an elbow and the support comprises an adjustable elbow apparatus.

18. The apparatus of claim 17, wherein the adjustable elbow apparatus comprises:
an upper arm prosthetic wearable on a proximal portion of the partial arm located adjacent the partial humerus bone;
a first elbow portion fixedly engageable with the upper arm prosthetic; and
a second elbow portion that is rotatably engageable with the first elbow portion and fixedly engageable with the terminal unit apparatus,
the force amplifier being rotatably engaged with upper arm prosthetic.

19. The apparatus of claim 18, wherein:
the first elbow portion comprises a semi-spherical connector element; and
the second elbow portion comprises a clamping element that is selectively engageable with the semi-spherical connector element to permit movement of the terminal unit apparatus relative to the upper arm prosthetic between different fixed positions.

20. The apparatus of claim 15, wherein the input member or the output member comprises one of a beam, a cable, a rod, a shaft, or wire.

* * * * *